(12) United States Patent
Lee et al.

(10) Patent No.: US 11,362,283 B2
(45) Date of Patent: Jun. 14, 2022

(54) ORGANIC ELECTROLUMINESCENT ELEMENT

(71) Applicant: LG Chem, Ltd., Seoul (KR)

(72) Inventors: Dae Woong Lee, Daejeon (KR); Yeon-Ho Cho, Daejeon (KR); Sang Young Jeon, Daejeon (KR); Hyoung Seok Kim, Daejeon (KR); Sang Duk Suh, Daejeon (KR)

(73) Assignee: LG Chem, Ltd.

( * ) Notice: Subject to any disclaimer, the term of this patent is extended or adjusted under 35 U.S.C. 154(b) by 457 days.

(21) Appl. No.: 15/554,881

(22) PCT Filed: Sep. 8, 2016

(86) PCT No.: PCT/KR2016/010092
§ 371 (c)(1),
(2) Date: Aug. 31, 2017

(87) PCT Pub. No.: WO2017/043887
PCT Pub. Date: Mar. 16, 2017

(65) Prior Publication Data
US 2018/0040829 A1  Feb. 8, 2018

(30) Foreign Application Priority Data
Sep. 9, 2015  (KR) ................. 10-2015-0127783

(51) Int. Cl.
| | | |
|---|---|---|
| H01L 51/52 | (2006.01) | |
| C07D 263/57 | (2006.01) | |
| C07D 277/66 | (2006.01) | |
| C07D 413/10 | (2006.01) | |
| C07D 413/14 | (2006.01) | |
| C07D 417/10 | (2006.01) | |
| C09K 11/06 | (2006.01) | |
| H01L 51/00 | (2006.01) | |
| H01L 51/50 | (2006.01) | |
| C09K 11/02 | (2006.01) | |

(52) U.S. Cl.
CPC ........ *H01L 51/0071* (2013.01); *C07D 263/57* (2013.01); *C07D 277/66* (2013.01); *C07D 413/10* (2013.01); *C07D 413/14* (2013.01); *C07D 417/10* (2013.01); *C09K 11/025* (2013.01); *C09K 11/06* (2013.01); *H01L 51/00* (2013.01); *H01L 51/006* (2013.01); *H01L 51/0056* (2013.01); *H01L 51/0058* (2013.01); *H01L 51/0061* (2013.01); *H01L 51/0067* (2013.01); *H01L 51/0072* (2013.01); *H01L 51/50* (2013.01); *H01L 51/52* (2013.01); *H01L 51/5275* (2013.01); *C09K 2211/1007* (2013.01); *C09K 2211/1011* (2013.01); *C09K 2211/1014* (2013.01); *C09K 2211/1029* (2013.01); *C09K 2211/1044* (2013.01); *C09K 2211/1092* (2013.01); *C09K 2211/185* (2013.01); *H01L 51/0052* (2013.01); *H01L 51/0054* (2013.01); *H01L 51/0059* (2013.01); *H01L 51/5012* (2013.01); *H01L 51/5016* (2013.01); *H01L 51/5028* (2013.01)

(58) Field of Classification Search
None
See application file for complete search history.

(56) References Cited

U.S. PATENT DOCUMENTS

| | | | | |
|---|---|---|---|---|
| 5,935,721 | A * | 8/1999 | Shi | ............... C09K 11/06 313/504 |
| 9,178,173 | B2 | 11/2015 | Birnstock et al. | |
| 2001/0000005 | A1* | 3/2001 | Forrest | ............... H01L 51/5234 204/192.12 |
| 2008/0023724 | A1 | 1/2008 | Takeda et al. | |
| 2009/0066245 | A1* | 3/2009 | Sugimoto | ........... H01L 51/0054 313/540 |
| 2009/0286985 | A1* | 11/2009 | Kadoma | ............... C07D 263/57 546/173 |
| 2012/0138918 | A1* | 6/2012 | Naraoka | ............... C09K 11/06 257/40 |

(Continued)

FOREIGN PATENT DOCUMENTS

| | | | |
|---|---|---|---|
| CN | 103022376 A | * | 4/2013 |
| CN | 104380842 A | | 2/2015 |

(Continued)

OTHER PUBLICATIONS

Yokoyama et al., Machine Translation of WO 2015/001726 A1, (2015), pp. 1-68. (Year: 2015).*
Li et al., Machine Translation of CN-103022376-A (2013) pp. 1-9. (Year: 2013).*
Ishiyama et al., Machine Translation of WO-2015141421-A1 (2015) pp. 1-11. (Year: 2015).*

(Continued)

*Primary Examiner* — Dylan C Kershner
(74) *Attorney, Agent, or Firm* — Lerner, David, Littenberg, Krumholz & Mentlik, LLP

(57) ABSTRACT

The present specification provides an organoluminescent device including a capping layer on one surface of an electrode, wherein the capping layer includes a compound represented by Chemical Formula 1:

[Chemical Formula 1]

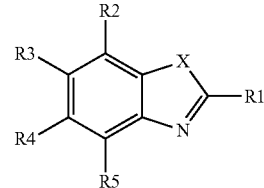

X, and R1 to R5 are defined therein.

15 Claims, 1 Drawing Sheet

(56) References Cited

U.S. PATENT DOCUMENTS

| | | | |
|---|---|---|---|
| 2013/0320307 A1* | 12/2013 | Birnstock | H01L 51/0071 257/40 |
| 2014/0225100 A1 | 8/2014 | Yokoyama et al. | |
| 2015/0041780 A1* | 2/2015 | Ma | H01L 51/0072 257/40 |
| 2015/0228907 A1* | 8/2015 | Ma | H01L 51/005 428/143 |
| 2015/0243895 A1 | 8/2015 | Lim et al. | |
| 2015/0287920 A1 | 10/2015 | Nagaoka et al. | |

FOREIGN PATENT DOCUMENTS

| | | | | |
|---|---|---|---|---|
| CN | 104860883 A | | 8/2015 | |
| JP | 2005113072 A | * | 4/2005 | |
| JP | 2005289921 A | * | 10/2005 | |
| JP | 2006302879 A | | 11/2006 | |
| JP | 201592485 A | | 5/2015 | |
| KR | 20120080536 A | | 7/2012 | |
| KR | 20130097093 A | | 9/2013 | |
| KR | 20140074928 A | | 6/2014 | |
| KR | 20140145370 A | | 12/2014 | |
| KR | 20150010016 A | | 1/2015 | |
| WO | 2015009076 A1 | | 1/2015 | |
| WO | WO-2015001726 A1 | * | 1/2015 | |
| WO | WO-2015141421 A1 | * | 9/2015 | C07C 69/54 |

OTHER PUBLICATIONS

Inoue et al., Machine translation of JP-2005289921-A (2005) pp. 1-21. (Year: 2005).*

Toba et al., Machine translation of JP-2005113072-A (2005) pp. 1-24. (Year: 2005).*

Chinese Search Report for Application No. 201680017178.4 dated Jul. 30, 2018.

Search report from International Application No. PCT/KR2016/010092, dated Dec. 14, 2016.

* cited by examiner

【FIG. 1】
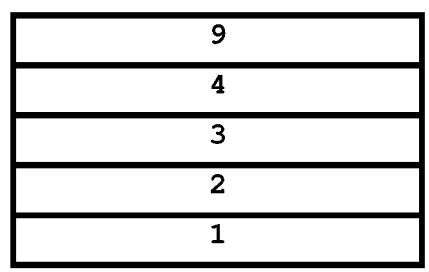
【FIG. 2】
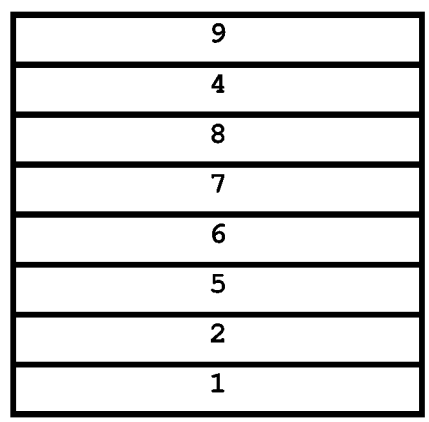

ORGANIC ELECTROLUMINESCENT ELEMENT

TECHNICAL FIELD

The present application is a national phase entry under 35 U.S.C. § 371 of International Application No. PCT/KR2016/010092 filed Sep. 8, 2016, published in Korean, which claims priority from Korean Patent Application No. 10-2015-01127783 filed on Sep. 9, 2015, all of which are incorporated herein by reference.

The present specification relates to an organoluminescent device.

BACKGROUND ART

An organic light emission phenomenon generally refers to a phenomenon converting electrical energy to light energy using an organic material. An organoluminescent device using an organic light emission phenomenon normally has a structure including an anode, a cathode, and an organic material layer therebetween. Herein, the organic material layer is often formed in a multilayer structure formed with different materials in order to increase efficiency and stability of the organoluminescent device, and for example, may be formed with a hole injection layer, a hole transfer layer, a light emitting layer, an electron transfer layer, an electron injection layer and the like. When a voltage is applied between the two electrodes in such an organoluminescent device structure, holes and electrons are injected to the organic material layer from the anode and the cathode, respectively, and when the injected holes and electrons meet, excitons are formed, and light emits when these excitons fall back to the ground state.

As displays using an organoluminescent device become to have large areas, solving problems of efficiency or lifespan has been required. Efficiency and lifespan, driving voltage and the like are related to each other, and as efficiency increases, driving voltage relatively decreases, and while driving voltage decreases, organic material crystallization caused by Joule heating produced during the driving becomes less resultantly leading to a lifespan increase.

Light efficiency of an organoluminescent device is commonly divided into internal luminescnet efficiency and external luminescent efficiency. Internal luminescnet efficiency relates to how efficiently excitons are produced in organic layers provided between a first electrode and a second electrode (that is, between an anode and a cathode) such as a hole transfer layer, a light emitting layer and an electron transfer layer, and light conversion is accomplished. Meanwhile, external luminescent efficiency (hereinafter, also referred to as "light coupling efficiency") indicates efficiency of light, which is produced in organic layers, extracted outside an organoluminescent device, and even when high light conversion efficiency is obtained in the organic layers (that is, even when internal luminescnet efficiency is high), overall light efficiency of the organoluminescent device is low when external luminescent efficiency is low.

Recently, organoluminescent devices having a top-emission structure emitting from the top using metals having large work function in an anode are being used, and in luminescent devices having a top-emission structure, a semi-transparent electrode such as LiF/Al/Ag, Ca/Mg and LiF/MgAg is used in a cathode. When light emitting to a light emitting layer enters into other layers in such organoluminescent devices, only a part of the emitting light may be used since the light is total-reflected at an interface between the light emitting layer and the other layers when the light enters at a certain angle or higher.

Accordingly, in order to enhance light coupling efficiency, organoluminescent devices in which a capping layer having a high refractive index is installed on an outer side of a semi-transparent electrode having a low refractive index have been proposed, and as a material of the capping layer, materials having a high refractive index, and having excellent thin film stability or durability have been required.

PRIOR ART DOCUMENTS

Patent Documents

Korean Patent Application Laid-Open Publication No. 2014-0145370

DISCLOSURE

Technical Problem

The present specification describes an organoluminescent device. The present disclosure is particularly directed to providing an organoluminescent device including a capping layer having high refractive index and heat resistance for improving light coupling efficiency of the organoluminescent device.

Technical Solution

One embodiment of the present specification provides an organoluminescent device including a first electrode; a second electrode; one or more organic material layers disposed between the first electrode and the second electrode; and a capping layer provided on, a surface opposite to a surface facing the organic material layers of surfaces of the first electrode and the second electrode, wherein the capping layer includes a compound represented by the following Chemical Formula 1.

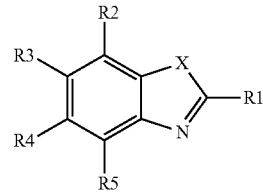

[Chemical Formula 1]

In Chemical Formula 1,
X is O or S,
R1 is represented by -(L1)p-A1,
L1 is a direct bond; a substituted or unsubstituted arylene group; or a substituted or unsubstituted heteroarylene group,
p is an integer of 0 to 10,
when p is 2 or greater, L is are the same as or different from each other,
A1 is a substituted or unsubstituted amine group; a substituted or unsubstituted aryl group; or a substituted or unsubstituted heterocyclic group,
R2 to R5 are the same as or different from each other, and each independently represented by -(L2)q-A2, or adjacent groups bond to each other to form a substituted or unsubstituted ring, L2 is a direct bond; a substituted or unsubstituted arylene group; or a substituted or unsubstituted heteroarylene group,
q is an integer of 0 to 10,
when q is 2 or greater, L2s are the same as or different from each other, and
A2 is hydrogen; deuterium; a substituted or unsubstituted aryl group; or a substituted or unsubstituted heterocyclic group.

Advantageous Effects

Compounds described in the present specification can be used as a material of an organic material layer of an organoluminescent device. Compounds according to at least one embodiment are capable of enhancing efficiency, low driving voltage and/or enhancing lifespan properties in an organoluminescent device. Particularly, light emission efficiency and color purity can be significantly improved in an organoluminescent device using compounds described in the present specification as a capping layer.

DESCRIPTION OF DRAWINGS

FIG. 1 illustrates an organoluminescent device in which a first electrode (2), an organic material layer (3), a second electrode (4) and a capping layer (9) are consecutively laminated on a substrate (1).

FIG. 2 illustrates an organoluminescent device in which a first electrode (2), a hole injection layer (5), a hole transfer layer (6), a light emitting layer (7), an electron transfer layer (8), a second electrode (4) and a capping layer (9) are consecutively laminated on a substrate (1).

1: Substrate
2: First Electrode
3: Organic Material Layer
4: Second Electrode
5: Hole Injection Layer
6: Hole Transfer Layer
7: Light Emitting Layer
8: Electron Transfer Layer
9: Capping Layer

MODE FOR DISCLOSURE

Hereinafter, the present specification will be described in more detail.

One embodiment of the present specification provides an organoluminescent device including a compound represented by Chemical Formula 1 in a capping layer.

Examples of the substituents are described below, however, the substituents are not limited thereto.

In the present specification, the term "substituted or unsubstituted" means being substituted with one or more substituents selected from the group consisting of deuterium; a halogen group; a nitrile group; a nitro group; a hydroxyl group; a carbonyl group; an ester group; an imide group; an amino group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; and a heterocyclic group, or being unsubstituted, or being substituted with a substituent linking two or more substituents among the substituents illustrated above, or being unsubstituted. For example, "a substituent linking two or more substituents" may include a biphenyl group. In other words, a biphenyl group may be an aryl group, or interpreted as a substituent linking two phenyl groups.

In the present specification, an "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other. Alternatively, a substituent substituting N in carbazole and a substituent of carbon number 2 or carbon number 8 in carbazole may be interpreted as an "adjacent group".

In the present specification, examples of the halogen group may include fluorine, chlorine, bromine or iodine.

In the present specification, the number of carbon atoms of the carbonyl group is not particularly limited, but is preferably from 1 to 40. Specifically, compounds having structures as below may be included, but the carbonyl group is not limited thereto.

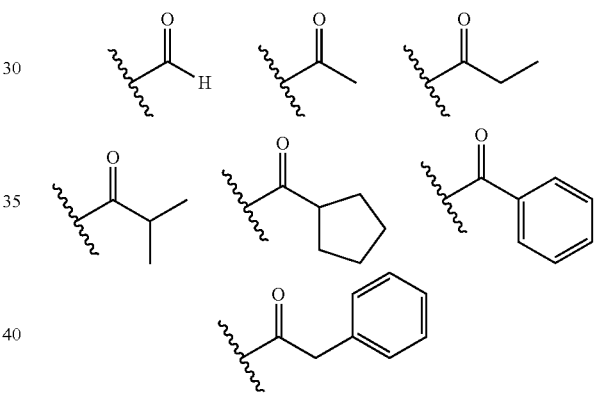

In the present specification, in the ester group, the oxygen of the ester group may be substituted with a linear, branched or cyclic alkyl group having 1 to 40 carbon atoms or an aryl group having 6 to 30 carbon atoms. Specifically, compounds having the following structural formulae may be included, but the ester group is not limited thereto.

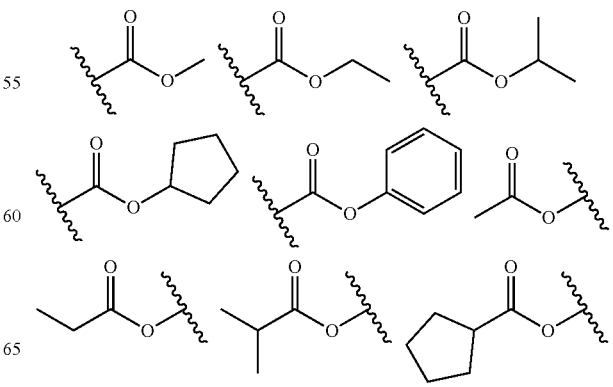

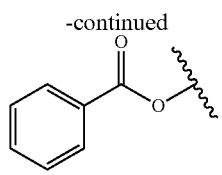

In the present specification, the number of carbon atoms of the imide group is not particularly limited, but is preferably from 1 to 25. Specifically, compounds having structures as below may be included, but the imide group is not limited thereto.

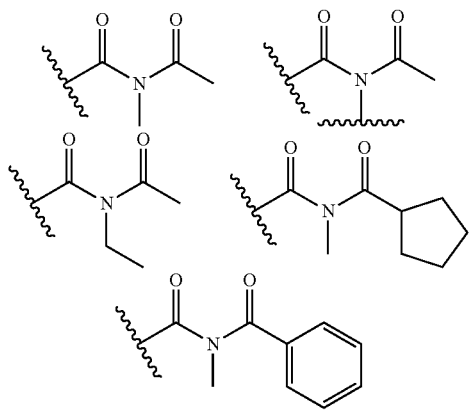

In the present specification, the silyl group may be represented by the chemical formula of —$SiR_aR_bR_c$, and $R_a$, $R_b$ and $R_c$ may each be hydrogen; a substituted or unsubstituted alkyl group; or a substituted or unsubstituted aryl group. Specific examples of the silyl group may include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the boron group may be represented by the chemical formula of —$BR_aR_b$, and $R_a$ and $R_b$ may each be hydrogen; a substituted or unsubstituted alkyl group; or a substituted or unsubstituted aryl group. Specific examples of the boron group may include a trimethylboron group, a triethylboron group, a t-butyldimethylboron group, a triphenylboron group, a phenylboron group and the like, but are not limited thereto.

In the present specification, the alkyl group may be linear or branched, and the number of carbon atoms is not particularly limited, but is preferably from 1 to 40. According to one embodiment, the number of carbon atoms of the alkyl group is from 1 to 20. According to another embodiment, the number of carbon atoms of the alkyl group is from 1 to 10. According to still another embodiment, the number of carbon atoms of the alkyl group is from 1 to 6. Specific examples of the alkyl group may include a methyl group, an ethyl group, a propyl group, an n-propyl group, an isopropyl group, a butyl group, an n-butyl group, an isobutyl group, a tert-butyl group, a sec-butyl group, a 1-methyl-butyl group, a 1-ethyl-butyl group, a pentyl group, an n-pentyl group, an isopentyl group, a neopentyl group, a tert-pentyl group, a hexyl group, an n-hexyl group, a 1-methylpentyl group, a 2-methylpentyl group, a 4-methyl-2-pentyl group, a 3,3-dimethylbutyl group, a 2-ethylbutyl group, a heptyl group, an n-heptyl group, a 1-methylhexyl group, a cyclopentylm-ethyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethyl-propyl group, a 1,1-dimethyl-propyl group, an isohexyl group, a 4-methylhexyl group, a 5-methylhexyl group and the like, but are not limited thereto.

In the present specification, the alkoxy group may be linear, branched or cyclic. The number of carbon atoms of the alkoxy group is not particularly limited, but is preferably from 1 to 40. Specific examples thereof may include a methoxy group, an ethoxy group, an n-propoxy group, an isopropoxy group, an i-propyloxy group, an n-butoxy group, an isobutoxy group, a tert-butoxy group, a sec-butoxy group, an n-pentyloxy group, a neopentyloxy group, an isopentyloxy group, an n-hexyloxy group, a 3,3-dimethylbutyloxy group, a 2-ethylbutyloxy group, an n-octyloxy group, an n-nonyloxy group, an n-decyloxy group, a benzyloxy group, a p-methylbenzyloxy group and the like, but are not limited thereto.

The alkyl group, the alkoxy group and other substituents including an alkyl group part described in the present specification include all of linear or branched forms.

In the present specification, the alkenyl group may be linear or branched, and although not particularly limited thereto, the number of carbon atoms is preferably from 2 to 40. According to one embodiment, the number of carbon atoms of the alkenyl group is from 2 to 20. According to another embodiment, the number of carbon atoms of the alkenyl group is from 2 to 10. According to still another embodiment, the number of carbon atoms of the alkenyl group is from 2 to 6. Specific examples thereof may include a vinyl group, a 1-propenyl group, an isopropenyl group, a 1-butenyl group, a 2-butenyl group, a 3-butenyl group, a 1-pentenyl group, a 2-pentenyl group, a 3-pentenyl group, a 3-methyl-1-butenyl group, a 1,3-butadienyl group, an allyl group, a 1-phenylvinyl-1-yl group, a 2-phenylvinyl-1-yl group, a 2,2-diphenylvinyl-1-yl group, a 2-phenyl-2-(naphthyl-1-yl)vinyl-1-yl group, a 2,2-bis(diphenyl-1-yl)vinyl-1-yl group, a stilbenyl group, a styrenyl group and the like, but are not limited thereto.

In the present specification, the cycloalkyl group is not particularly limited, but preferably has 3 to 60 carbon atoms, and according to one embodiment, the number of carbon atoms of the cycloalkyl group is from 3 to 40. According to another embodiment, the number of carbon atoms of the cycloalkyl group is from 3 to 20. According to still another embodiment, the number of carbon atoms of the cycloalkyl group is from 3 to 6. Specific examples thereof may include a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4-methylcyclohexyl group, a 2,3-dimethylcyclohexyl group, a 3,4,5-trimethylcyclohexyl group, a 4-tert-butylcyclohexyl group, a cycloheptyl group, a cyclooctyl group and the like, but are not limited thereto.

In the present specification, the number of carbon atoms of the alkylamine group is not particularly limited, but is preferably from 1 to 40. Specific examples of the alkylamine group may include a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, a phenylnaphthylamine group, a ditolylamine group, a phenyltolylamine group, a triphenylamine group and the like, but are not limited thereto.

In the present specification, examples of the arylamine group may include a substituted or unsubstituted monoarylamine group, a substituted or unsubstituted diarylamine group, or a substituted or unsubstituted triarylamine group. The aryl group in the arylamine group may be a monocyclic aryl group or a multicyclic aryl group. The arylamine group including two or more aryl groups may include monocyclic aryl groups, multicyclic aryl groups, or both monocyclic aryl groups and multicyclic aryl groups.

Specific examples of the arylamine group may include a phenylamine group, a naphthylamine group, a biphenylamine group, an anthracenylamine group, a 3-methyl-phenylamine group, a 4-methyl-naphthylamine group, a 2-methyl-biphenylamine group, a 9-methyl-anthracenylamine group, a diphenylamine group, a phenylnaphthylamine group, a ditolylamine group, a phenyltolylamine group, carbozole, a triphenylamine group and the like, but are not limited thereto.

In the present specification, examples of the heteroarylamine group include a substituted or unsubstituted monoheteroarylamine group, a substituted or unsubstituted diheteroarylamine group, or a substituted or unsubstituted triheteroarylamine group. The heteroaryl group in the heteroarylamine group may be a monocyclic heterocyclic group or a multicyclic heterocyclic group. The heteroarylamine group including two or more heterocyclic groups may include monocyclic heterocyclic groups, multicyclic heterocyclic groups, or both monocyclic heterocyclic groups and multicyclic heterocyclic groups.

In the present specification, the arylheteroarylamine group means an amine group substituted with an aryl group and a heterocyclic group.

In the present specification, examples of the arylphosphine group include a substituted or unsubstituted monoarylphosphine group, a substituted or unsubstituted diarylphosphine group, or a substituted or unsubstituted triarylphosphine group. The aryl group in the arylphosphine group may be a monocyclic aryl group or a multicyclic aryl group. The arylphosphine group including two or more aryl groups may include monocyclic aryl groups, multicyclic aryl groups, or both monocyclic aryl groups and multicyclic aryl groups.

In the present specification, the aryl group is not particularly limited, but preferably has 6 to 60 carbon atoms, and may be a monocyclic aryl group or a multicyclic aryl group. According to one embodiment, the number of carbon atoms of the aryl group is from 6 to 30. According to one embodiment, the number of carbon atoms of the aryl group is from 6 to 20. Examples of the monocyclic aryl group may include a phenyl group, a biphenyl group, a terphenyl group, a quaterphenyl group, a quinquephenyl group and the like, but are not limited thereto. Examples of the multicyclic aryl group may include a naphthyl group, an anthracenyl group, a phenanthryl group, a pyrenyl group, a perylenyl group, a chrysenyl group, a fluorenyl group and the like, but are not limited thereto.

In the present specification, the fluorenyl group may be substituted, and two of the substituents may bond to each other to form a spiro structure.

When the fluorenyl group is substituted, spirofluorenyl groups such as

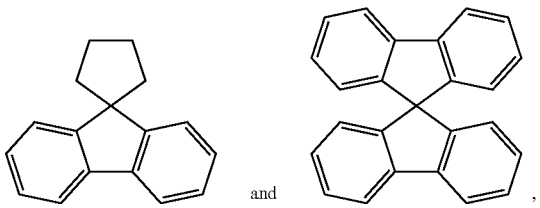

and substituted fluorenyl groups such as

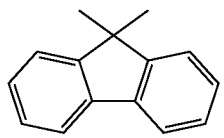

(9,9-dimethylfluorenyl group), and

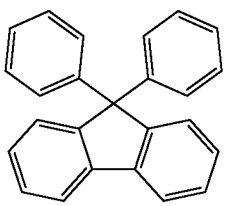 [SMILES: c1ccc(C2(c3ccccc3)c3ccccc3-c3ccccc32)cc1]

(9,9-diphenylfluorenyl group) may be included. However, the compounds are not limited thereto.

In the present specification, the heterocyclic group is a heterocyclic group including one or more of N, O, P, S, Si and Se as a heteroatom, and although not particularly limited thereto, the number of carbon atoms is preferably from 1 to 60. According to one embodiment, the number of carbon atoms of the heterocyclic group is from 1 to 30. Examples of the heterocyclic group may include a pyridyl group, a pyrrole group, pyrimidyl group, a pyridazinyl group, a furanyl group, a thiophenyl group, an imidazole group, a pyrazole group, an oxazole group, an isoxazole group, a triazole group, an isothiazole group, a triazole group, an oxadiazole group, a thiadiazole group, a dithiazole group, a tetrazole group, a pyranyl group, a thiopyranyl group, a pyrazinyl group, an oxazinyl group, a thiazinyl group, a dioxinyl group, a triazinyl group, a tetrazinyl group, a quinolinyl group, an isoquinolinyl group, a quinolyl group, a quinazolinyl group, a quinoxalinyl group, a naphthyridinyl group, an acridyl group, a xanthenyl group, a phenanthridinyl group, a diazanaphthalenyl group, a triazaindenyl group, an indole group, an indolinyl group, an indolizinyl group, a phthalazinyl group, a pyridopyrimidinyl group, a pyridopyrazinyl group, a pyrazinopyrazinyl group, a benzothiazole group, a benzoxazole group, a benzimidazole group, a benzothiophene group, a benzofuranyl group, a dibenzothiophenyl group, a dibenzofuranyl group, a carbazole group, a benzocarbazole group, a dibenzocarbazole group, an indolocarbazole group, an indenocarbazole group, a phenazinyl group, an imidazopyridine group, a phenoxazinyl group, a phenanthridine group, a phenanthroline group, a phenothiazine group, an imidazopyridine group, an imidazophenanthridine group, a benzimidazoquinazoline group, a benzimidazophenanthridine group or the like, but are not limited thereto.

In the present specification, the descriptions on the heterocyclic group provided above may be used on the heteroaryl group except that the heteroaryl group is an aromatic group.

In the present specification, the descriptions on the aryl group provided above may be used on the aryl group in the aryloxy group, the arylthioxy group, the arylsulfoxy group, the arylphosphine group, the aralkyl group, the aralkylamine group, the aralkenyl group, the alkylaryl group, the arylamine group and the arylheteroarylamine group.

In the present specification, the descriptions on the alkyl group provided above may be used on the alkyl group in the alkylthioxy group, the alkylsulfoxy group, the aralkyl group, the aralkylamine group, the alkylaryl group and the alkylamine group.

In the present specification, the descriptions on the heterocyclic group provided above may be used on the heteroaryl group in the heteroaryl group, the heteroarylamine group and the arylheteroarylamine group.

In the present specification, the descriptions on the alkenyl group provided above may be used on the alkenyl group in the aralkenyl group.

In the present specification, the descriptions on the aryl group provided above may be used on the arylene group except that the arylene group is divalent.

In the present specification, the descriptions on the heterocyclic group provided above may be used on the heteroarylene group except that the heteroarylene group is divalent.

In the present specification, adjacent groups binding to each other to form a ring means adjacent groups binding to each other to form a substituted or unsubstituted aliphatic hydrocarbon ring; a substituted or unsubstituted aromatic hydrocarbon ring; a substituted or unsubstituted aliphatic heteroring; a substituted or unsubstituted aromatic heteroring; or a fused ring thereof.

In the present specification, the aliphatic hydrocarbon ring means a ring formed only with carbon and hydrogen atoms as a ring that is not aromatic. Specific examples of the aliphatic hydrocarbon ring may include cyclopropane, cyclobutane, cyclobutene, cyclopentane, cyclopentene, cyclohexane, cyclohexene, 1,4-cyclohexadiene, cycloheptane, cycloheptene, cyclooctane, cyclooctene and the like, but are not limited thereto.

In the present specification, the aromatic hydrocarbon ring is an aromatic ring formed only with carbon and hydrogen atoms. Specific examples of the aromatic hydrocarbon ring may include a benzene group, a naphthalene group, an anthracene group, a phenanthrene group, a perylene group, a fluoranthene group, a triphenylene group, a phenalene group, a pyrene group, a tetracene group, a chrysene group, a pentacene group, a fluorene group, an indene group, an acetnaphthalene group, a benzofluorene group, a spirofluorene group and the like, but are not limited thereto.

In the present specification, the aliphatic heteroring means an aliphatic ring including one or more of heteroatoms. Specific examples of the aliphatic heteroring may include an oxirane group, a tetrahydrofuran group, a 1,4-dioxane group, a pyrrolidine group, a piperidine group, a morpholine group, an oxetane group, an azoxane group, a thioxane group and the like, but are not limited thereto.

In the present specification, the aromatic heteroring means an aromatic ring including one or more of heteroatoms. Specific examples of the aromatic heteroring may include a pyridine group, a pyrrole group, a pyrimidine group, a pyridazine group, a furan group, a thiophene group, an imidazole group, a pyrazole group, an oxazole group, an isoxazole group, a triazole group, an isothiazole group, a triazole group, an oxadiazole group, a thiadiazole group, a dithiazole group, a tetrazole group, a pyran group, a thiopyran group, a diazine group, an oxazine group, a triazine group, a dioxine group, a triazine group, a tetrazine group, an isoquinoline group, a quinoline group, a quinol group, a quinazoline group, a quinoxaline group, a naphthyridine group, an acridine group, a phenanthridine group, a diazanaphthalene group, a triazaindene group, an indole group, an indolizine group, a benzothiazole group, a benzoxazole group, a benzimidazole group, a benzothiophene group, a benzofuran group, a dibenzothiophene group, a dibenzofuran group, a carbazole group, a benzocarbazole group, a dibenzocarbazole group, a phenazine group, an imidazopyridine group, a phenoxazine group, a phenanthridine group, an indolocarbazole group, an indenocarbazole group and the like, but are not limited thereto.

In the present specification, the aliphatic hydrocarbon ring, the aromatic hydrocarbon ring, the aliphatic heteroring and the aromatic heteroring may be monocyclic or multicyclic.

According to one embodiment of the present specification, the compound represented by Chemical Formula 1 may be represented by the following Chemical Formula 2 or Chemical Formula 3.

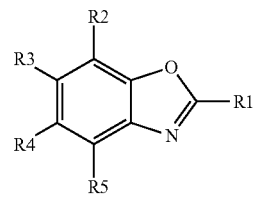

[Chemical Formula 2]

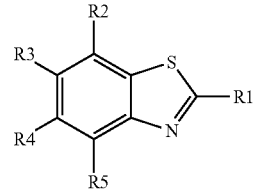

[Chemical Formula 3]

In Chemical Formula 2 or Chemical Formula 3, definitions of R1 to R5 are the same as in Chemical Formula 1.

In one embodiment of the present disclosure, L1 is a direct bond; a substituted or unsubstituted arylene group having 6 to 60 carbon atoms; or a substituted or unsubstituted heteroarylene group having 1 to 60 carbon atoms.

In one embodiment of the present disclosure, L1 is a direct bond; a monocyclic or multicyclic substituted or unsubstituted arylene group having 6 to 30 carbon atoms; or a monocyclic or multicyclic substituted or unsubstituted heteroarylene group having 1 to 30 carbon atoms.

In one embodiment of the present disclosure, L1 is a direct bond; a substituted or unsubstituted phenylene group; a substituted or unsubstituted biphenylylene group; a substituted or unsubstituted terphenylene group; a substituted or unsubstituted quaterphenylene group; a substituted or unsubstituted naphthylene group; a substituted or unsubstituted anthracenylene group; a substituted or unsubstituted phenanthrenylene group; a substituted or unsubstituted triphenylenylene group; a substituted or unsubstituted pyrenylene group; or a substituted or unsubstituted fluorenylene group; a substituted or unsubstituted pyridinylene group; a substituted or unsubstituted pyrimidinylene group; a substituted or unsubstituted triazinylene group; a substituted or unsubstituted quinolinylene group; a substituted or unsubstituted isoquinolinylene group; a substituted or unsubstituted quinazolinylene group; a substituted or unsubstituted quinoxalinylene group; a substituted or unsubstituted benzimidazole group; a substituted or unsubstituted benzoxazole group; a substituted or unsubstituted benzothiazole group; a substituted or unsubstituted dibenzofuranylene group; a substituted or unsubstituted dibenzothiophenylene group; or a substituted or unsubstituted carbazolylene group.

In one embodiment, L1 is a direct bond; or a substituted or unsubstituted arylene group.

In one embodiment, L1 is a direct bond; a substituted or unsubstituted phenylene group; a substituted or unsubstituted biphenylylene group; or a substituted or unsubstituted naphthylene group.

According to one embodiment of the present specification, the compound represented by Chemical Formula 1 may be represented by the following Chemical Formula 4 to Chemical Formula 11.

[Chemical Formula 4]

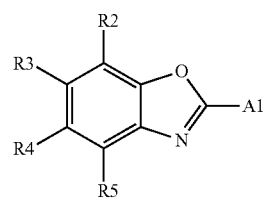

[Chemical Formula 5]

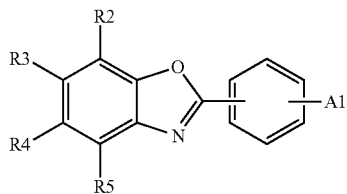

[Chemical Formula 6]

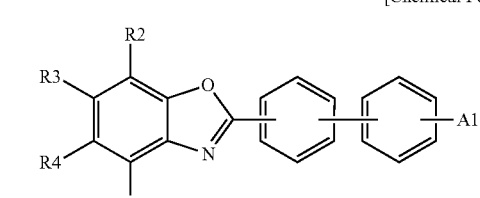

[Chemical Formula 7]

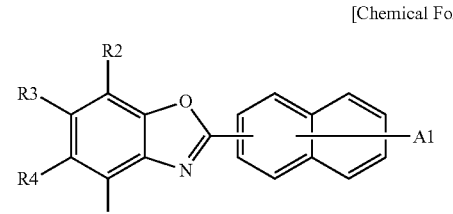

[Chemical Formula 8]

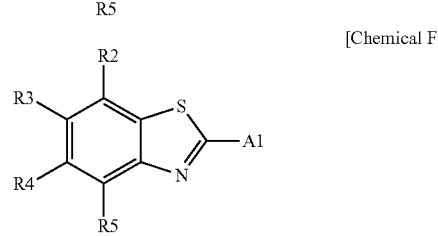

[Chemical Formula 9]

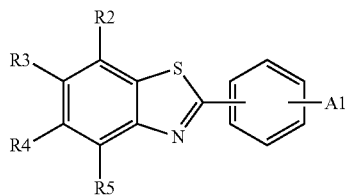

[Chemical Formula 10]

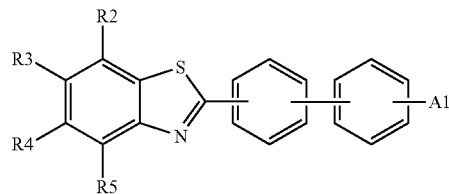

[Chemical Formula 11]

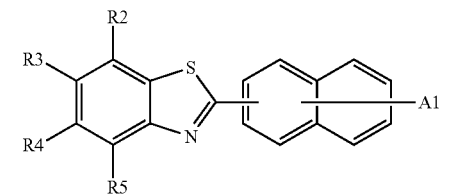

In Chemical Formula 4 to Chemical Formula 11,
definitions of R2 to R5 and A1 are the same as in Chemical Formula 1.

In one embodiment of the present disclosure, A1 is a substituted or unsubstituted amine group; a substituted or unsubstituted aryl group; or a substituted or unsubstituted heterocyclic group.

In one embodiment of the present disclosure, A1 is a substituted or unsubstituted alkylamine group having 1 to 40 carbon atoms; a substituted or unsubstituted arylamine group having 6 to 60 carbon atoms; a substituted or unsubstituted heteroarylamine group having 1 to 60 carbon atoms; a substituted or unsubstituted aryl group having 6 to 60 carbon atoms; or a substituted or unsubstituted heterocyclic group having 1 to 60 carbon atoms.

In one embodiment of the present disclosure, A1 is an alkylamine group such as a substituted or unsubstituted methylamine group; a substituted or unsubstituted dimethylamine group; a substituted or unsubstituted ethylamine group; a substituted or unsubstituted diethylamine group; or a substituted or unsubstituted phenylamine group, an arylamine group such as a substituted or unsubstituted phenylamine group; a substituted or unsubstituted biphenylamine group; a substituted or unsubstituted naphthylamine group; a substituted or unsubstituted anthracenylamine group; a substituted or unsubstituted fluoreneamine group; a substituted or unsubstituted diphenylamine group; a substituted or unsubstituted phenylbiphenylamine group; a substituted or unsubstituted phenylnaphthylamine group; a substituted or unsubstituted ditolylamine group; or a substituted or unsubstituted triphenylamine group, a heteroarylamine group such as a substituted or unsubstituted pyridineamine group; a substituted or unsubstituted pyrazineamine group; a substituted or unsubstituted benzothiazoleamine group; or a substituted or unsubstituted benzoxazoleamine group, an aryl group such as a substituted or unsubstituted phenyl group; a substituted or unsubstituted biphenyl group; a substituted or unsubstituted terphenyl group; a substituted or unsubstituted quaterphenyl group; a substituted or unsubstituted quinquephenyl group; a substituted or unsubstituted naphthyl group; a substituted or unsubstituted anthracenyl group; a substituted or unsubstituted chrysenyl group; a substituted or unsubstituted phenanthrenyl group; a substituted or unsubstituted triperylenyl group; a substituted or unsubstituted pyrenyl group; a substituted or unsubstituted tetracenyl group; a substituted or unsubstituted pentacenyl group; or a substituted or unsubstituted fluorenyl group, or a heterocyclic group such as a substituted or unsubstituted pyrimidyl group; a substituted or unsubstituted pyrimidinyl group; a substituted or unsubstituted triazinyl group; a substituted or unsubstituted quinolinyl group; a substituted or unsubstituted isoquinolinyl group; a substituted or unsubstituted quinazolinyl group; a substituted or unsubstituted quinoxalinyl group; a substituted or unsubstituted naphthyridinyl group; a substituted or unsubstituted acridyl group; a substituted or unsubstituted xanthenyl group; a substituted or unsubstituted phenanthridinyl group; a substituted or unsubstituted diazanaphthalenyl group; a substituted or unsubstituted triazaindenyl group; a substituted or unsubstituted indole group; a substituted or unsubstituted indolinyl group; a substituted or unsubstituted indolizinyl group; a substituted or unsubstituted phthalazinyl group; a substituted or unsubstituted benzimidazole group; a substituted or unsubstituted benzoxazole group; a substituted or unsubstituted benzothiazole group; a substituted or unsubstituted pyridopyrimidinyl group; a substituted or unsubstituted pyridopyrazinyl group; a substituted or unsubstituted pyrazinopyrazinyl group; a substituted or unsubstituted carbazolyl group; a substituted or unsubstituted benzothiophene group; a substituted or unsubstituted benzofuranyl group; a substituted or unsubstituted benzocarbazolyl group; a substituted or unsubstituted naphthobenzothiophene group; a substituted or unsubstituted naphthobenzofuranyl group; a substituted or unsubstituted dibenzocarbazolyl group; a substituted or unsubstituted indolocarbazolyl group; a substituted or unsubstituted indenocarbazolyl group; a substituted or unsubstituted phenanthroline group; a substituted or unsubstituted phenazinyl group; a substituted or unsubstituted phenoxazinyl group; a substituted or unsubstituted phenothiazinyl group; a substituted or unsubstituted imidazopyridinyl group; a substituted or unsubstituted imidazophenanthridine group; a substituted or unsubstituted benzimidazoquinazolinyl group; or a substituted or unsubstituted benzimidazophenanthridinyl group.

In one embodiment of the present disclosure, L2 is a direct bond; a substituted or unsubstituted arylene group having 6 to 60 carbon atoms; or a substituted or unsubstituted heteroarylene group having 1 to 60 carbon atoms.

In one embodiment of the present disclosure, L2 is a direct bond; a monocyclic or multicyclic substituted or unsubstituted arylene group having 6 to 30 carbon atoms; or a monocyclic or multicyclic substituted or unsubstituted heteroarylene group having 1 to 30 carbon atoms.

In one embodiment of the present disclosure, L2 is a direct bond; a substituted or unsubstituted phenylene group; a substituted or unsubstituted biphenylylene group; a substituted or unsubstituted terphenylene group; a substituted or unsubstituted quaterphenylene group; a substituted or unsubstituted naphthylene group; a substituted or unsubstituted anthracenylene group; a substituted or unsubstituted phenanthrenylene group; a substituted or unsubstituted triphenylenylene group; a substituted or unsubstituted pyrenylene group; or a substituted or unsubstituted fluorenylene group; a substituted or unsubstituted pyridinylene group; a substituted or unsubstituted pyrimidinylene group; a substituted or unsubstituted triazinylene group; a substituted or unsubstituted quinolinylene group; a substituted or unsubstituted isoquinolinylene group; a substituted or unsubstituted quinazolinylene group; a substituted or unsubstituted quinoxalinylene group; a substituted or unsubstituted benzimidazole group; a substituted or unsubstituted benzoxazole group; a substituted or unsubstituted benzothiazole group; a substituted or unsubstituted dibenzofuranylene group; a substituted or unsubstituted dibenzothiophenylene group; or a substituted or unsubstituted carbazolylene group.

In one embodiment, L2 is a direct bond; or a substituted or unsubstituted arylene group.

In one embodiment, L2 is a direct bond; a substituted or unsubstituted phenylene group; a substituted or unsubstituted biphenylylene group; or a substituted or unsubstituted naphthylene group.

According to one embodiment of the present specification, the compound represented by Chemical Formula 1 may be represented by the following Chemical Formula 12 to Chemical Formula 19.

[Chemical Formula 12]

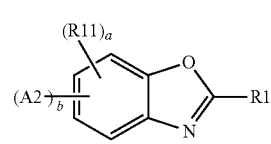

[Chemical Formula 13]

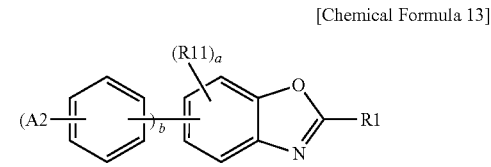

[Chemical Formula 14]

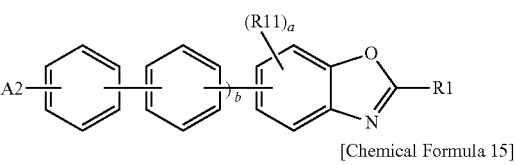

[Chemical Formula 15]

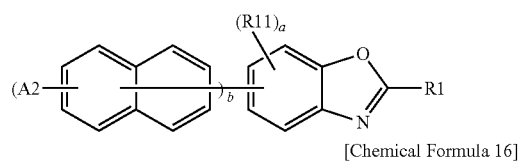

[Chemical Formula 16]

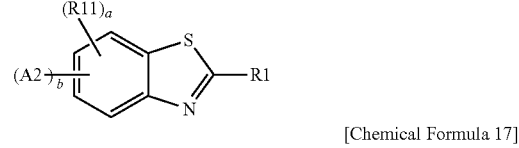

[Chemical Formula 17]

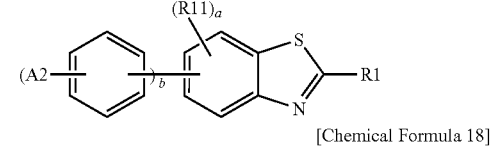

[Chemical Formula 18]

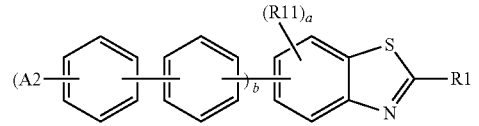

-continued

[Chemical Formula 19]

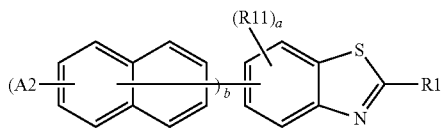

In Chemical Formula 12 to Chemical Formula 19,

R11 has the same definition as R2 to R5 in Chemical Formula 1, definitions of R1 and A2 are the same as in Chemical Formula 1, a and b are the same as or different from each other, and each independently an integer of 0 to 4, and a+b is 4.

In one embodiment of the present disclosure, A2 is hydrogen; deuterium; a substituted or unsubstituted aryl group; or a substituted or unsubstituted heterocyclic group.

In one embodiment of the present disclosure, A2 is hydrogen; deuterium; a substituted or unsubstituted aryl group having 6 to 60 carbon atoms; or a substituted or unsubstituted heterocyclic group having 1 to 60 carbon atoms.

In one embodiment of the present disclosure, A2 is hydrogen; deuterium; a substituted or unsubstituted monocyclic or multicyclic aryl group having 6 to 30 carbon atoms; or a substituted or unsubstituted monocyclic or multicyclic heterocyclic group having 1 to 60 carbon atoms.

In one embodiment, A2 is hydrogen; deuterium; an aryl group such as a substituted or unsubstituted phenyl group; a substituted or unsubstituted biphenyl group; a substituted or unsubstituted terphenyl group; a substituted or unsubstituted quaterphenyl group; a substituted or unsubstituted quinquephenyl group; a substituted or unsubstituted naphthyl group; a substituted or unsubstituted anthracenyl group; a substituted or unsubstituted chrysenyl group; a substituted or unsubstituted phenanthrenyl group; a substituted or unsubstituted triperylenyl group; a substituted or unsubstituted pyrenyl group; a substituted or unsubstituted tetracenyl group; a substituted or unsubstituted pentacenyl group; or a substituted or unsubstituted fluorenyl group, or a heterocyclic group such as a substituted or unsubstituted pyrimidyl group; a substituted or unsubstituted pyrimidinyl group; a substituted or unsubstituted triazinyl group; a substituted or unsubstituted quinolinyl group; a substituted or unsubstituted isoquinolinyl group; a substituted or unsubstituted quinazolinyl group; a substituted or unsubstituted quinoxalinyl group; a substituted or unsubstituted naphthyridinyl group; a substituted or unsubstituted acridyl group; a substituted or unsubstituted xanthenyl group; a substituted or unsubstituted phenanthridinyl group; a substituted or unsubstituted diazanaphthalenyl group; a substituted or unsubstituted triazaindenyl group; a substituted or unsubstituted indole group; a substituted or unsubstituted indolinyl group; a substituted or unsubstituted indolizinyl group; a substituted or unsubstituted phthalazinyl group; a substituted or unsubstituted benzimidazole group; a substituted or unsubstituted benzoxazole group; a substituted or unsubstituted benzothiazole group; a substituted or unsubstituted pyridopyrimidinyl group; a substituted or unsubstituted pyridopyrazinyl group; a substituted or unsubstituted pyrazinopyrazinyl group; a substituted or unsubstituted carbazolyl group; a substituted or unsubstituted benzothiophene group; a substituted or unsubstituted benzothiophene group; a substituted or unsubstituted benzofuranyl group; a substituted or unsubstituted benzocarbazolyl group; a substituted or unsubstituted naphthobenzothiophene group; a substituted or unsubstituted naphthobenzofuranyl group; a substituted or unsubstituted dibenzocarbazolyl group; a substituted or unsubstituted indolocarbazolyl group; a substituted or unsubstituted indenocarbazolyl group; a substituted or unsubstituted phenanthroline group; a substituted or unsubstituted phenazinyl group; a substituted or unsubstituted phenoxazinyl group; a substituted or unsubstituted phenothiazinyl group; a substituted or unsubstituted imidazopyridinyl group; a substituted or unsubstituted imidazophenanthridine group; a substituted or unsubstituted benzimidazoquinazolinyl group; or a substituted or unsubstituted benzimidazophenanthridinyl group.

In another embodiment, adjacent groups among R2 to R5 may bond to each other to form an aliphatic substituted or unsubstituted ring or an aromatic substituted or unsubstituted ring.

In one embodiment, adjacent groups among R2 to R5 may bond to each other to form an aliphatic substituted or unsubstituted hydrocarbon ring; an aromatic substituted or unsubstituted hydrocarbon ring; an aliphatic substituted or unsubstituted heteroring; or an aromatic substituted or unsubstituted heteroring.

In one embodiment, adjacent groups among R2 to R5 may bond to each other to form an aliphatic hydrocarbon ring such as substituted or unsubstituted cyclopropane; substituted or unsubstituted cyclobutane; substituted or unsubstituted cyclobutene; substituted or unsubstituted cyclopentane; substituted or unsubstituted cyclopentene; substituted or unsubstituted cyclohexane; substituted or unsubstituted cyclohexene; substituted or unsubstituted 1,4-cyclohexadiene; substituted or unsubstituted cycloheptane; substituted or unsubstituted cycloheptene; substituted or unsubstituted cyclooctane; or substituted or unsubstituted cyclooctene, an aromatic hydrocarbon ring such as substituted or unsubstituted benzene; substituted or unsubstituted naphthalene; substituted or unsubstituted anthracene; substituted or unsubstituted phenanthrene; substituted or unsubstituted perylene; substituted or unsubstituted fluoranthene; substituted or unsubstituted triphenylene; substituted or unsubstituted phenalene; substituted or unsubstituted pyrene; substituted or unsubstituted tetracene; substituted or unsubstituted chrysene; substituted or unsubstituted pentacene; substituted or unsubstituted fluorene; substituted or unsubstituted indene; substituted or unsubstituted acetnaphthylene; substituted or unsubstituted benzofluorene; or substituted or unsubstituted spirofluorene, an aliphatic heteroring group such as substituted or unsubstituted oxirane; substituted or unsubstituted tetrahydrofuran; substituted or unsubstituted 1,4-dioxane; substituted or unsubstituted pyrrolidine; substituted or unsubstituted piperidine; substituted or unsubstituted morpholine; substituted or unsubstituted oxetane; substituted or unsubstituted azoxane; or substituted or unsubstituted thioxane, or an aromatic heteroring such as substituted or unsubstituted pyridine; substituted or unsubstituted pyrrole; substituted or unsubstituted pyrimidine; substituted or unsubstituted pyridazine; substituted or unsubstituted furan; substituted or unsubstituted thiophene; substituted or unsubstituted imidazole; substituted or unsubstituted pyrazole; substituted or unsubstituted oxazole; substituted or unsubstituted isoxazole; substituted or unsubstituted triazole; substituted or unsubstituted isothiazole; substituted or unsubstituted triazole; substituted or unsubstituted oxadiazole; substituted or unsubstituted thiadiazole; substituted or unsubstituted dithiazole; substituted or unsubstituted tetrazole; substituted or unsubstituted pyran; substituted or unsubstituted thiopyran; substituted or unsubstituted diazine; substituted or unsubstituted oxazine; substituted or unsubstituted triazine; substituted or unsubstituted dioxine; substituted or unsubstituted triazine; substituted or unsubstituted tetrazine; substituted or unsubstituted isoquinoline; substituted or unsubstituted quinoline; substituted or unsubstituted quinol; substituted or unsubstituted quinazoline; substituted or unsubstituted quinoxaline; substituted or unsubstituted naphthyridine; substituted or unsubstituted acridine; substituted or unsubstituted phenanthridine; substituted or unsubstituted diazanaphthalene; substituted or unsubstituted triazaindene; substituted or unsubstituted indole; substituted or unsubstituted indolizine; substituted or unsubstituted benzothiazole; substituted or unsubstituted benzoxazole; substituted or unsubstituted benzimidazole; substituted or unsubstituted benzothiophene; substituted or unsubstituted benzofuran; substituted or unsubstituted dibenzothiophene; substituted or unsubstituted dibenzofuran; substituted or unsubstituted carbazole; substituted or unsubstituted benzocarbazole; substituted or unsubstituted dibenzocarbazole; substituted or unsubstituted phenazine; substituted or unsubstituted imidazopyridine; substituted or unsubstituted phenoxazine; substituted or unsubstituted phenanthridine; substituted or unsubstituted indolocarbazole; or substituted or unsubstituted indenocarbazole.

In one embodiment of the present disclosure, the compound of Chemical Formula 1 may be any one selected from among the following compounds, and the following compounds may be further substituted.

Formula 1-1

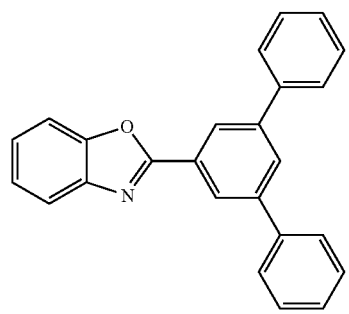

Formula 1-2

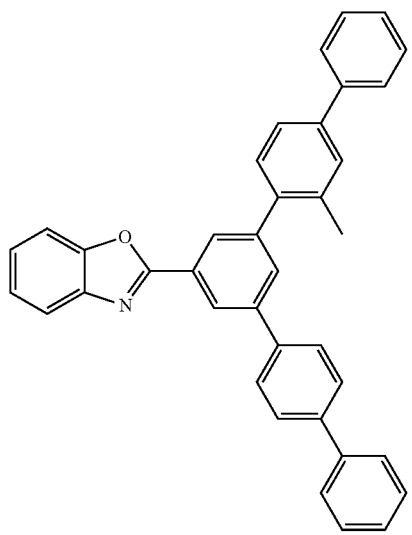

Formula 1-3

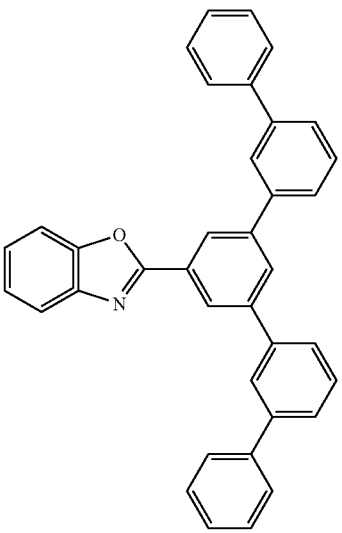

Formula 1-4

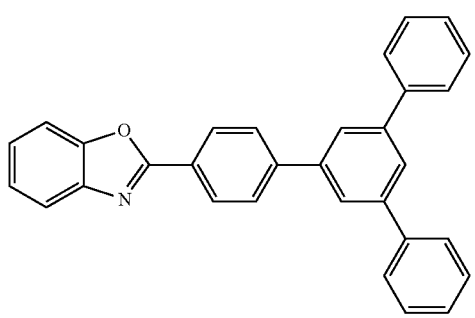

Formula 1-5

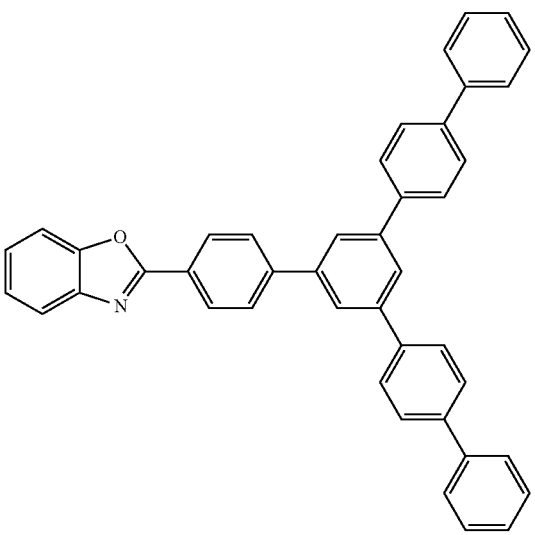

Formula 1-6
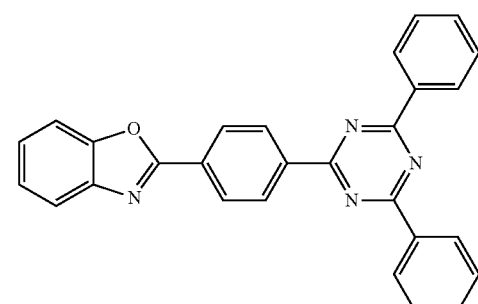
Formula 1-7
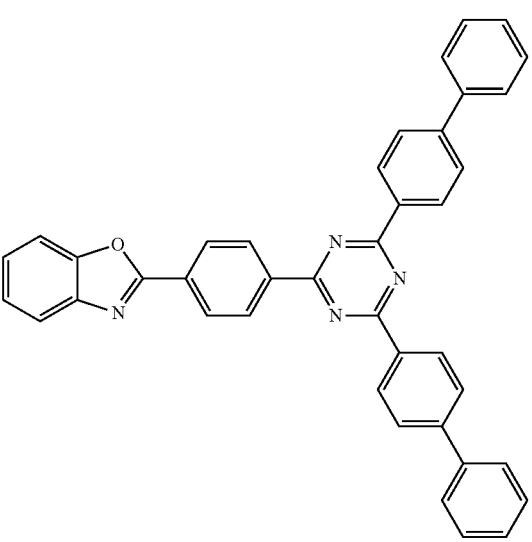
Formula 1-8
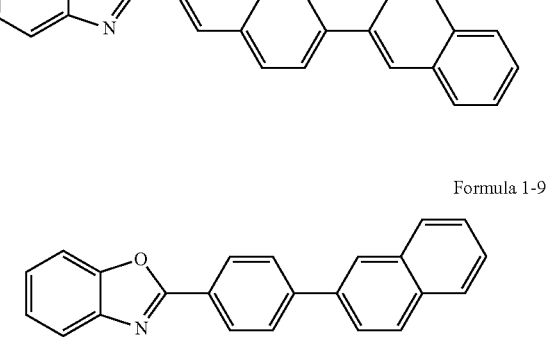
Formula 1-9
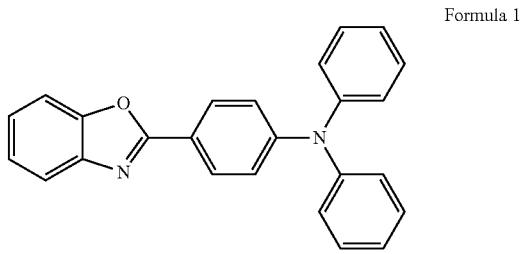
Formula 1-10
Formula 1-11
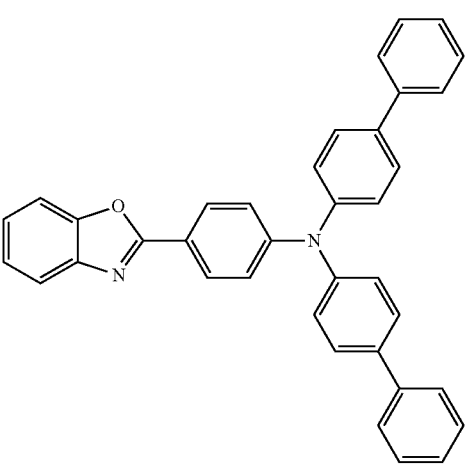
Formula 1-12
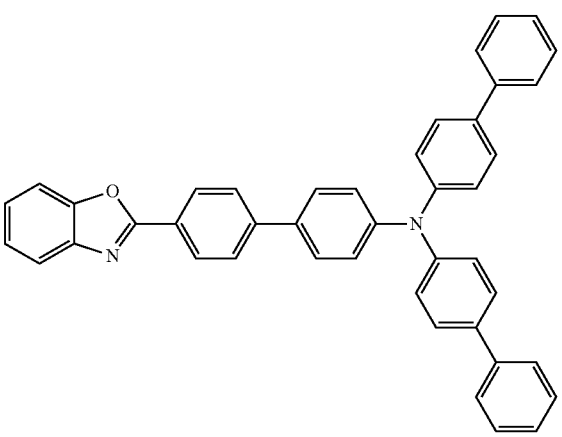
Formula 1-13
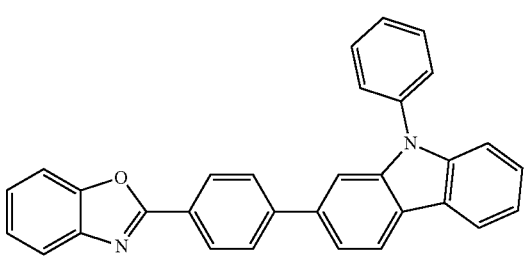
Formula 1-14
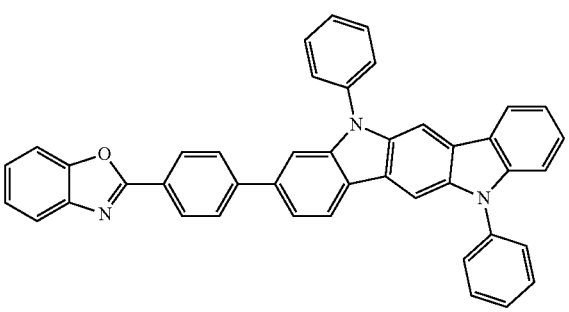

Formula 1-15
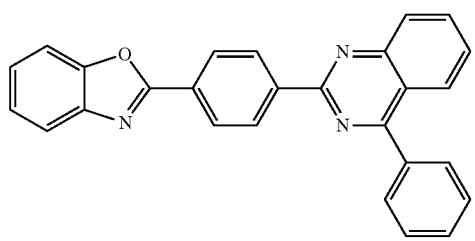
Formula 1-16
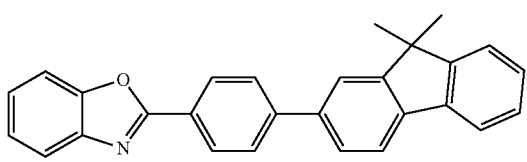
Formula 1-17
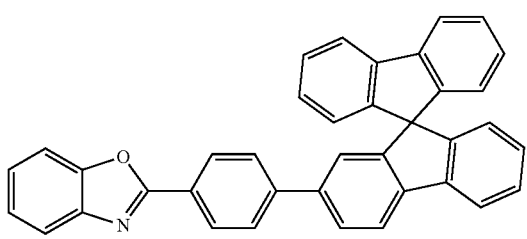
Formula 1-18
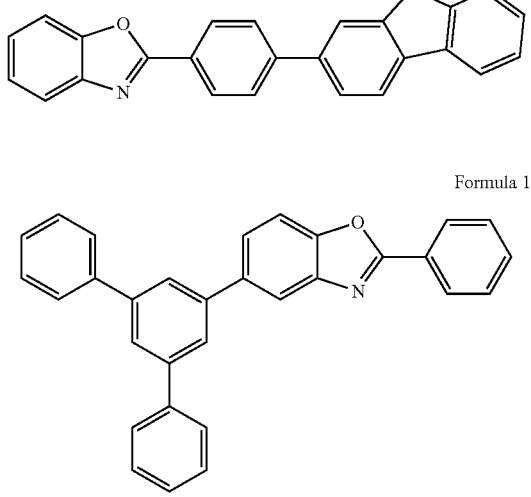
Formula 1-19
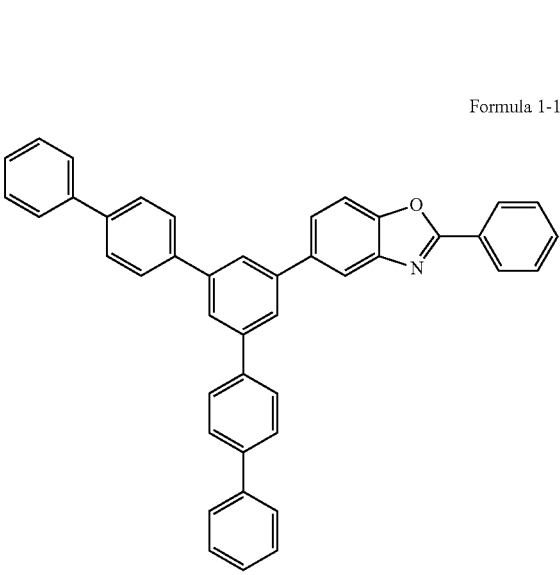
Formula 1-20
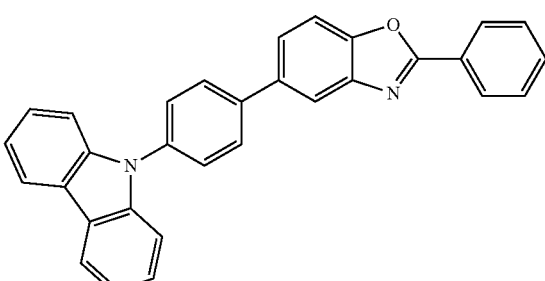
Formula 1-21
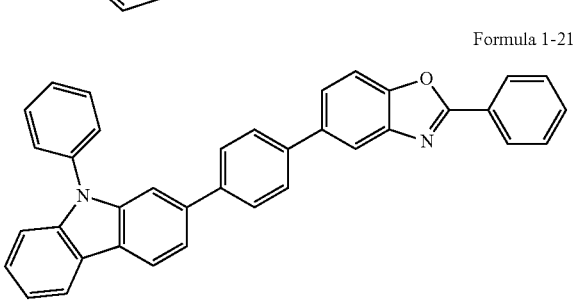
Formula 1-22
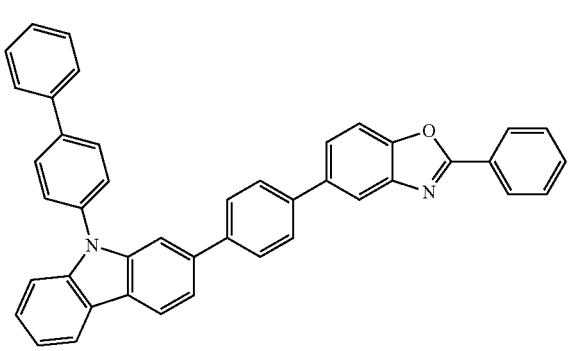
Formula 1-23
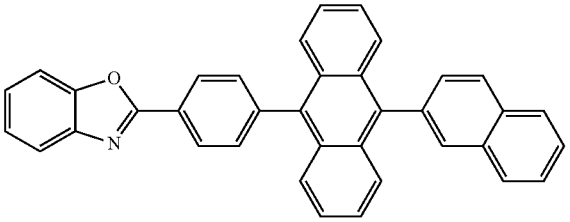
Formula 1-24
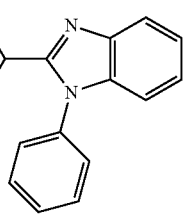

-continued
Formula 1-25
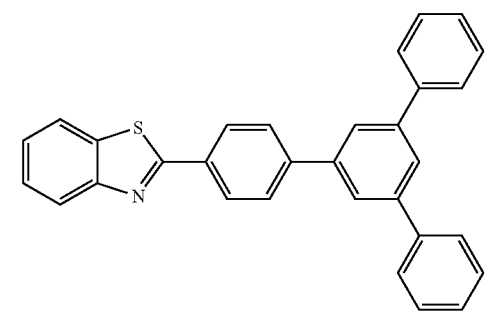
Formula 1-26
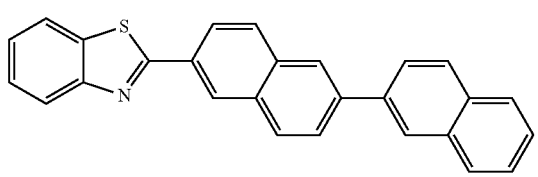
Formula 1-27
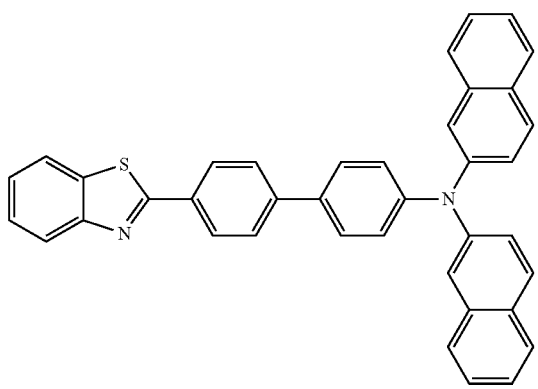
Formula 1-28
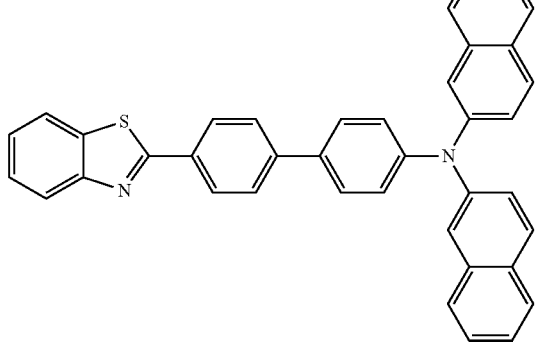
Formula 1-29
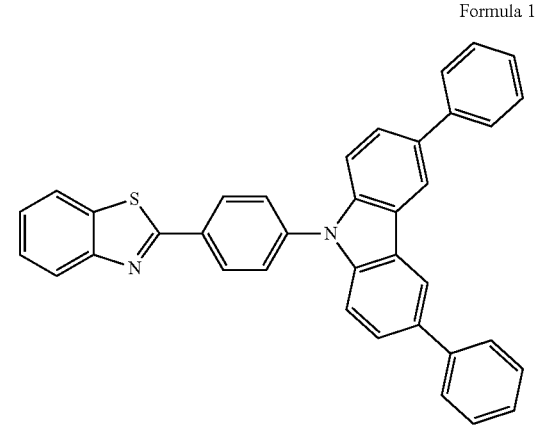
-continued
Formula 1-30
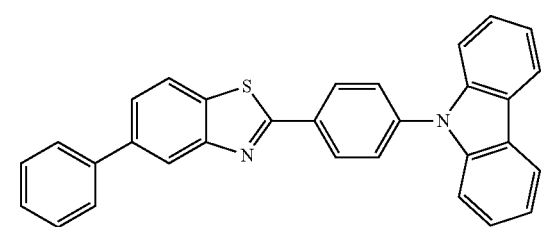
Formula 1-31
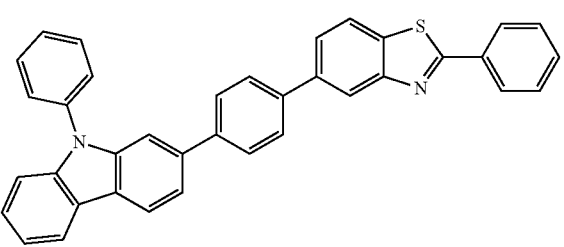
Formula 1-32
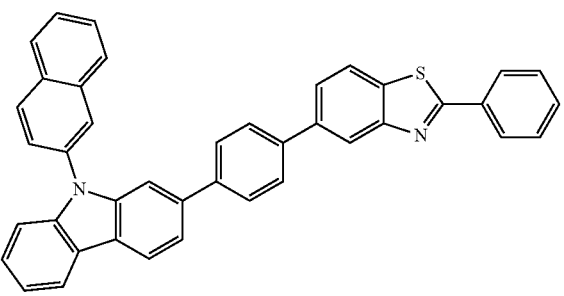
Formula 1-33
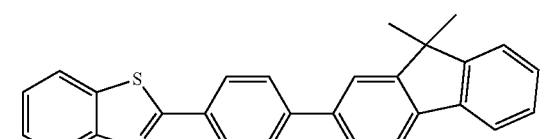
Formula 1-34
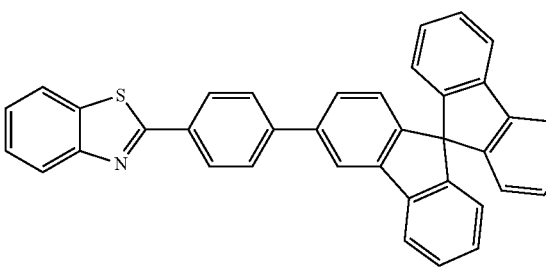
Formula 1-35
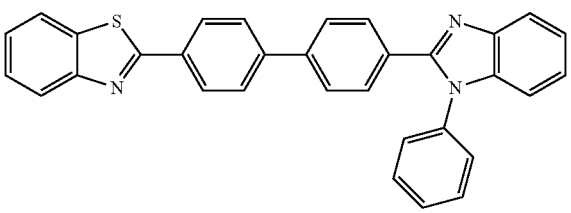

Formula 1-36
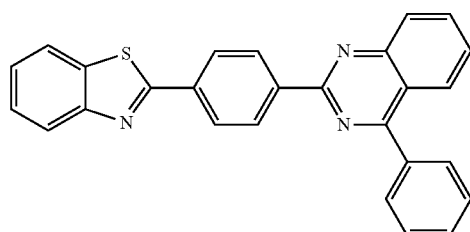
Formula 1-37
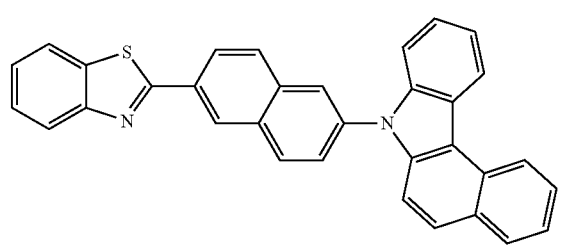
Formula 1-38
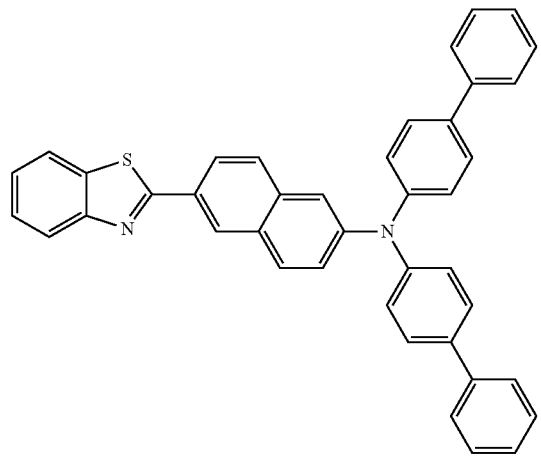
Formula 1-39
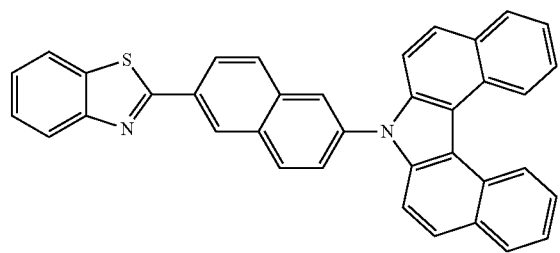
Formula 1-40
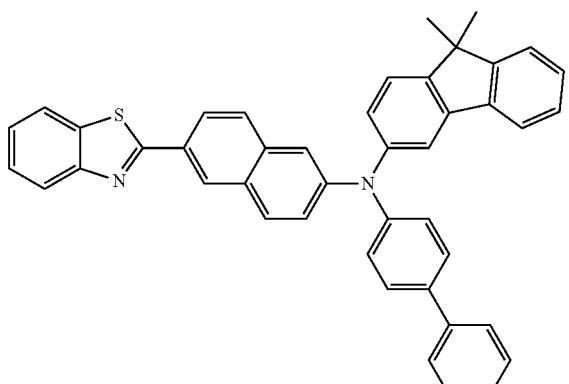
Formula 1-41
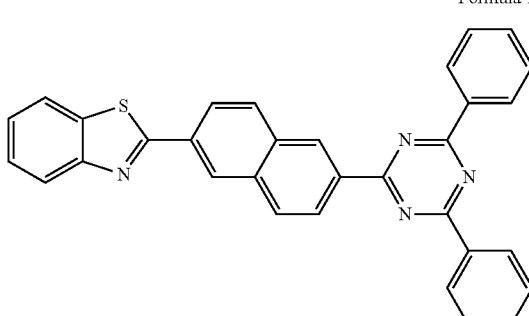
Formula 1-42
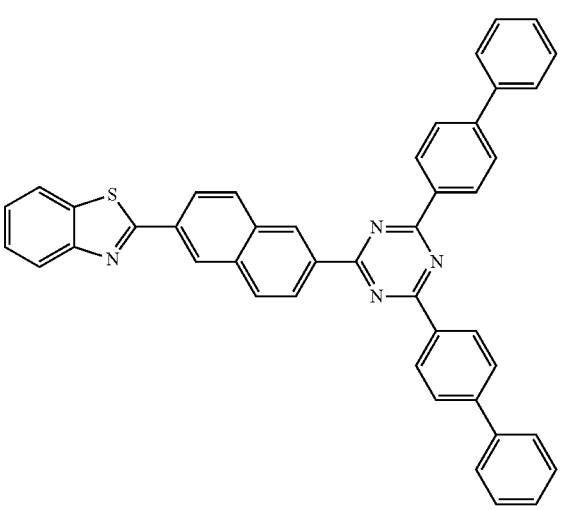
Formula 1-43
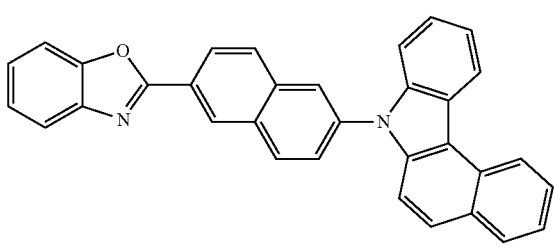

Formula 1-44
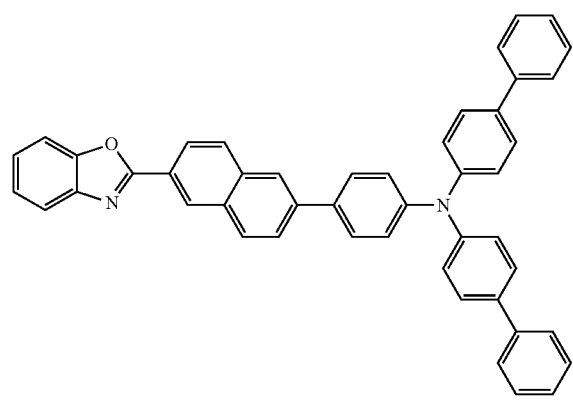
Formula 1-45
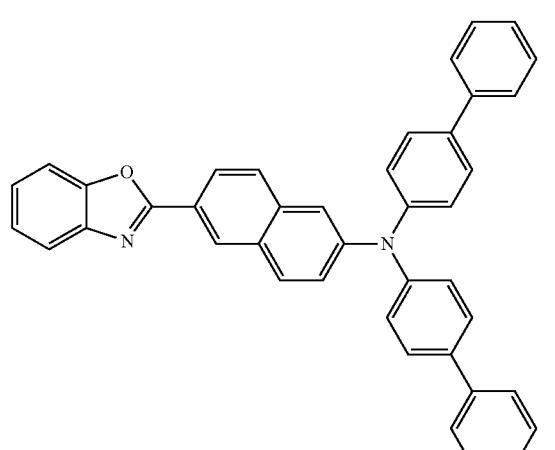
Formula 1-46
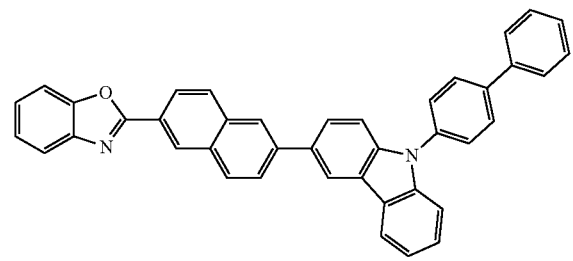
Formula 1-47
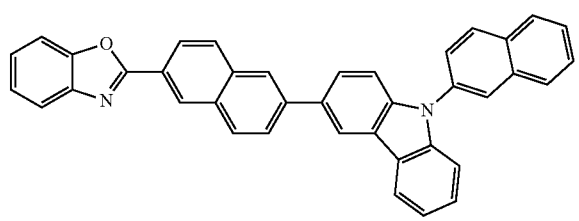
Formula 1-48
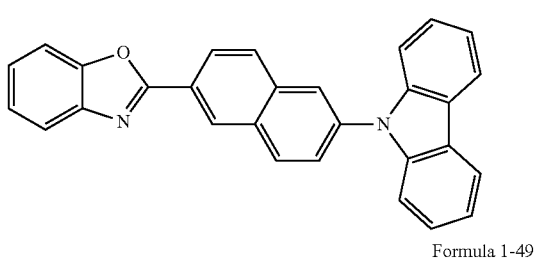
Formula 1-49
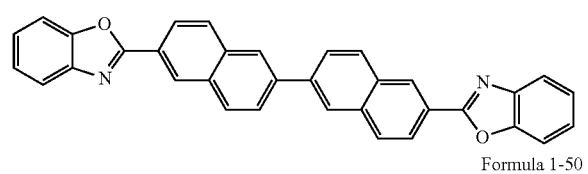
Formula 1-50
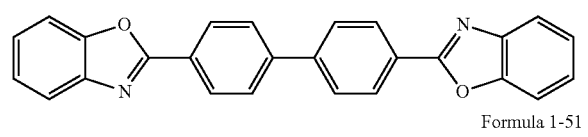
Formula 1-51
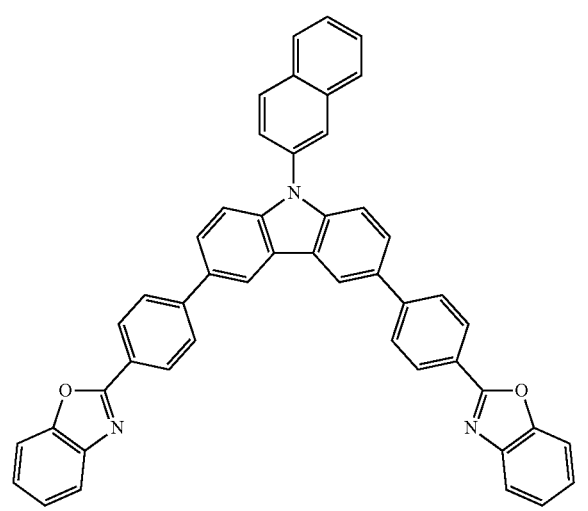
Formula 1-52
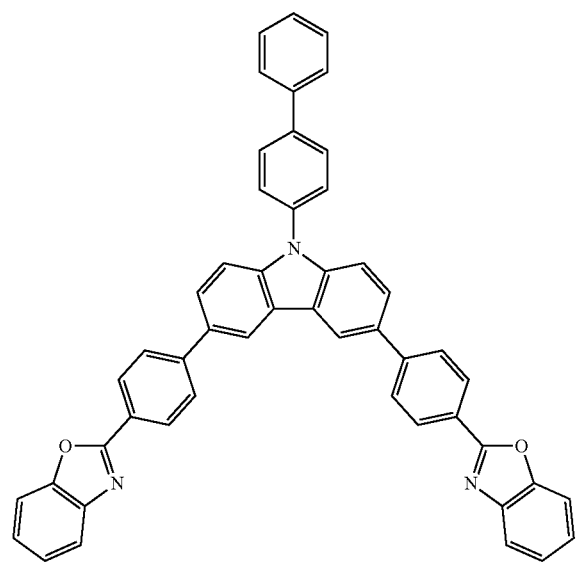

Formula 1-53

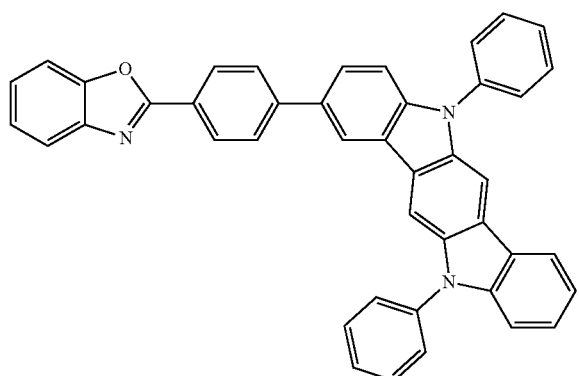

Formula 1-54

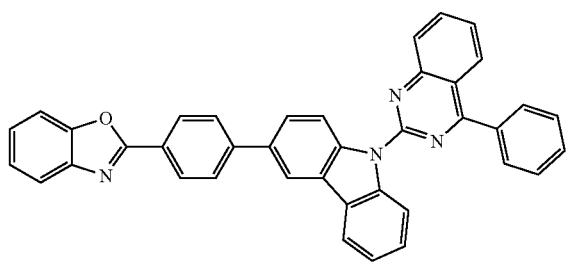

Formula 1-55

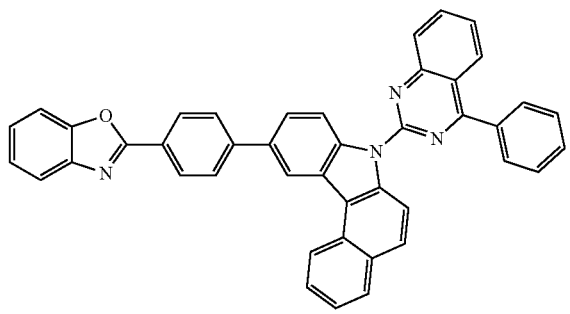

Formula 1-56

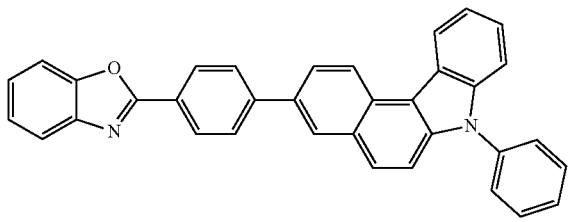

Formula 1-57

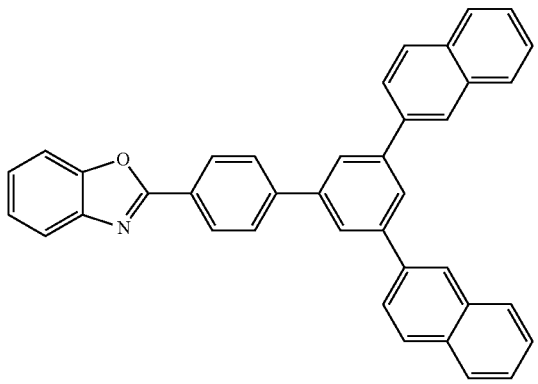

Specifically, the structures may be unsubstituted or substituted with one or more substituents selected from the group consisting of deuterium; a halogen group; a nitrile group; a nitro group; a hydroxyl group; a carbonyl group; an ester group; an imide group; an amine group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylheteroarylamine group; arylphosphine group; and a heterocyclic group.

An organoluminescent device according to the present disclosure includes a first electrode, a second electrode, one or more organic material layers disposed between the first electrode and the second electrode, and a capping layer provided on, a surface opposite to a surface facing the organic material layers of surfaces of the first electrode and the second electrode, wherein the capping layer includes the compound of Chemical Formula 1.

In one embodiment, the organic material layer includes a light emitting layer.

In another embodiment, the organic material layer may include one or more layers of an electron injection layer, an electron transfer layer, a hole injection layer, a hole transfer layer, and a layer carrying out hole injection and hole transfer at the same time.

In one embodiment, the organic material layer includes a light emitting layer, and the light emitting layer includes a compound represented by the following Chemical Formula A-1.

[Chemical Formula A-1]

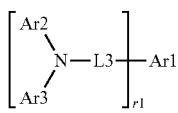

In Chemical Formula A-1,
r1 is an integer of 1 or greater,
Ar1 is a substituted or unsubstituted monovalent or higher benzofluorene group; a substituted or unsubstituted monovalent or higher fluoranthene group; a substituted or unsubstituted monovalent or higher pyren group; or a substituted or unsubstituted monovalent or higher chrysene group, L3 is a direct bond; a substituted or unsubstituted arylene group; or a substituted or unsubstituted heteroarylene group, Ar2 and Ar3 are the same as or different from each other, and each independently a substituted or unsubstituted aryl group; a substituted or unsubstituted silyl group; a substituted or unsubstituted alkyl group; a substituted or unsubstituted arylalkyl group; or a substituted or unsubstituted a heteroaryl group, or bond to each other to form a substituted or unsubstituted ring, when r1 is 2 or greater, structures in the parentheses are the same as or different from each other.

In one embodiment, the organic material layer includes a light emitting layer, and the light emitting layer includes the compound represented by Chemical Formula A-1 as a dopant of the light emitting layer.

According to one embodiment, L3 is a direct bond.

According to one embodiment, r1 is 2.

In one embodiment, Ar1 is a divalent pyren group unsubstituted or substituted with deuterium, a methyl group, an ethyl group, an isopropyl group or a tert-butyl group; or a divalent chrysene group unsubstituted or substituted with deuterium, a methyl group, an ethyl group, an isopropyl group or a tert-butyl group.

In one embodiment, Ar1 is a divalent pyren group unsubstituted or substituted with a methyl group.

According to one embodiment, Ar2 and Ar3 are the same as or different from each other, and each independently a substituted or unsubstituted aryl group having 6 to 30 carbon atoms.

According to one embodiment, Ar2 and Ar3 are the same as or different from each other, and each independently an aryl group unsubstituted or substituted with an alkyl group.

In one embodiment, Ar2 and Ar3 are the same as or different from each other, and each independently an aryl group unsubstituted or substituted with a methyl group, an ethyl group or an isopropyl group.

According to one embodiment, Ar2 and Ar3 are the same as or different from each other, and each independently a phenyl group unsubstituted or substituted with a methyl group.

According to one embodiment, Ar2 and Ar3 are the same as or different from each other, and each independently a biphenyl group unsubstituted or substituted with a methyl group.

According to one embodiment, Ar2 and Ar3 are the same as or different from each other, and each independently a terphenyl group unsubstituted or substituted with a methyl group.

In one embodiment, Chemical Formula A-1 is selected from among the following compounds.

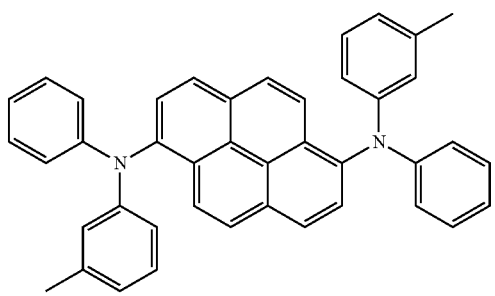

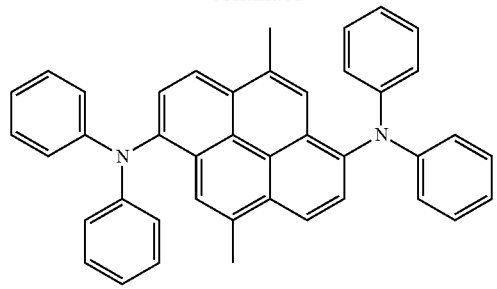

In one embodiment, the organic material layer includes a light emitting layer, and the light emitting layer includes a compound represented by the following Chemical Formula A-2.

[Chemical Formula A-2]

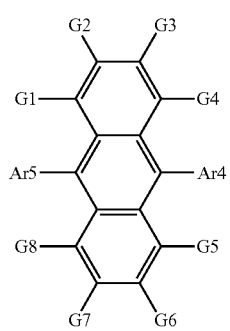

In Chemical Formula A-2,

Ar4 and Ar5 are the same as or different from each other, and each independently a substituted or unsubstituted monocyclic aryl group; or a substituted or unsubstituted multicyclic aryl group, G1 to G8 are the same as or different from each other, and each independently hydrogen; a substituted or unsubstituted monocyclic aryl group; or a substituted or unsubstituted multicyclic aryl group.

In one embodiment, the organic material layer includes a light emitting layer, and the light emitting layer includes the compound represented by Chemical Formula A-2 as a host of the light emitting layer.

In one embodiment of the present disclosure, Ar4 and Ar5 are the same as or different from each other, and each independently a substituted or unsubstituted multicyclic aryl group.

In one embodiment, Ar4 and Ar5 are the same as or different from each other, and each independently a substituted or unsubstituted naphthyl group.

In one embodiment of the present disclosure, Ar4 and Ar5 are the same as or different from each other, and each independently a substituted or unsubstituted 2-naphthyl group.

According to one embodiment, Ar4 and Ar5 are a 2-naphthyl group.

In one embodiment, G1 to G8 are the same as or different from each other, and each independently hydrogen; or a substituted or unsubstituted multicyclic aryl group.

According to one embodiment, G1 to G8 are the same as or different from each other, and each independently hydrogen; or a substituted or unsubstituted multicyclic aryl group having 6 to 30 carbon atoms.

In one embodiment of the present disclosure, G1 to G8 are the same as or different from each other, and each independently hydrogen; or a substituted or unsubstituted naphthyl group.

In one embodiment, G1 to G8 are the same as or different from each other, and each independently hydrogen; or a naphthyl group unsubstituted or substituted with an aryl group.

In one embodiment, G1 to G8 are the same as or different from each other, and each independently hydrogen; or a naphthyl group substituted with a 9-phenylanthracenyl group.

In one embodiment of the present disclosure, Chemical Formula A-2 is selected from among the following compounds.

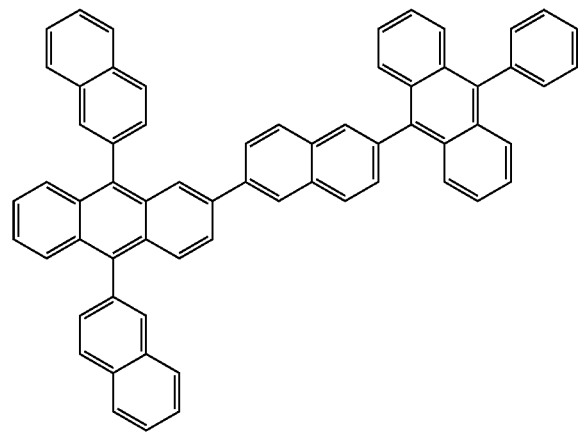 [SMILES: c1ccc(-c2c3ccccc3c(-c3ccc4cc(-c5ccc6c(-c7ccc8ccccc8c7)c7ccccc7c(-c7ccc8ccccc8c7)c6c5)ccc4c3)c3ccccc23)cc1]

In one embodiment, the organic material layer includes a light emitting layer, and the light emitting layer includes the compound represented by Chemical Formula A-1 as a dopant of the light emitting layer, and includes the compound represented by Chemical Formula A-2 as a host of the light emitting layer.

The organoluminescent device of the present disclosure may be manufactured using common methods and materials for manufacturing organoluminescent devices, except that a capping layer is formed using the compounds described above.

The compound may be formed into the capping layer using a solution coating method as well as a vacuum deposition method when manufacturing an organoluminescent device. Herein, the solution coating method means spin coating, dip coating, ink jet printing, screen printing, a spray method, roll coating and the like, but is not limited thereto.

The organic material layer of the organoluminescent device may be formed in a single layer structure, but may be formed in a multilayer structure in which two or more organic material layers are laminated. For example, the organoluminescent device of the present disclosure may have a structure including a hole injection layer, a hole transfer layer, a light emitting layer, an electron transfer layer, an electron injection layer and the like as the organic material layer. However, the structure of the organoluminescent device is not limited thereto, and may include less numbers of organic material layers.

For example, the organoluminescent device of the present disclosure may have structures as shown in FIG. 1 and FIG. 2, however, the structure is not limited thereto.

FIG. 1 illustrates a structure of an organoluminescent device in which a first electrode (2), an organic material layer (3), a second electrode (4) and a capping layer (9) are consecutively laminated on a substrate (1). In such a structure, the compound may be included in the capping layer (9).

FIG. 2 illustrates a structure of an organoluminescent device in which a first electrode (2), a hole injection layer (5), a hole transfer layer (6), a light emitting layer (7), an electron transfer layer (8), a second electrode (4) and a capping layer (9) are consecutively laminated on a substrate (1). In such a structure, the compound may be included in the capping layer (9).

For example, the organoluminescent device according to the present disclosure may be manufactured by forming an anode on a substrate by depositing a metal, a metal oxide having conductivity, or an alloy thereof using a physical vapor deposition (PVD) method such as sputtering or e-beam evaporation, forming an organic material layer including a hole injection layer, a hole transfer layer, a light emitting layer and an electron transfer layer thereon, and then depositing a material capable of being used as a cathode thereon, and a capping layer including the compound of Chemical Formula 1 may be formed thereon to improve light coupling efficiency. In addition to such a method, the organoluminescent device may also manufactured by forming a capping layer on a substrate, and then consecutively depositing a cathode material, an organic material layer, and an anode material thereon.

The organic material layer may have a multilayer structure including a hole injection layer, a hole transfer layer, a light emitting layer, an electron transfer layer and the like, but is not limited thereto, and may have a single layer structure. In addition, the organic material layer may be prepared into less numbers of layers using various polymer materials through a solvent process such as spin coating, dip coating, doctor blading, screen printing, ink jet printing or a thermal transfer method instead of a deposition method.

As the anode material, materials having large work function are normally preferable so that hole injection to an organic material layer is smooth. Specific examples of the anode material capable of being used in the present disclosure include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or SnO$_2$:Sb; conductive polymers such as poly(3-methyl compound), poly[3,4-(ethylene-1,2-dioxy)compound] (PEDT), polypyrrole and polyaniline, but are not limited thereto.

As the cathode material, materials having small work function are normally preferable so that electron injection to an organic material layer is smooth. Specific examples of the cathode material include metals such as magnesium, calcium, sodium, potassium, titanium, indium, yttrium, lithium, gadolinium, aluminum, silver, tin and lead, or alloys thereof; multilayer structure materials such as LiF/Al or LiO$_2$/Al, and the like, but are not limited thereto.

As the hole injection material, materials having a highest occupied molecular orbital (HOMO) between the work function of an anode material and the HOMO of surrounding organic material layers are preferable as materials favorably receiving holes from an anode at a low voltage. Specific examples of the hole injection material include metal porphyrins, oligothiophene, arylamine-based organic materials, hexanitrile hexazatriphenylene-based organic materials, quinacridone-based organic materials, perylene-based organic materials, anthraquinone, and polyaniline- and polythiophene-based conductive polymers, and the like, but are not limited thereto.

As the hole injection material, known hole injections materials may be used, and examples thereof may include phthalocyanine compounds such as copper phthalocyanine, 4,4',4''-tris(3-methylphenylphenylamino)triphenylamine (m-MTDATA), N,N'-di(1-naphthyl)-N,N'-diphenylbenzidine (NPB), TDATA, 2T-NATA, polyaniline/dodecylbenzenesulfonic acid (PANI/DBSA), poly(3,4-ethylenedioxythiophene)/poly(4-styrenesulfonate) (PEDOT/PSS), polyaniline/camphor sulfonic acid (PANI/CSA), polyaniline/poly(4-styrenesulfonate) (PANI/PSS) or the like, but are not limited thereto.

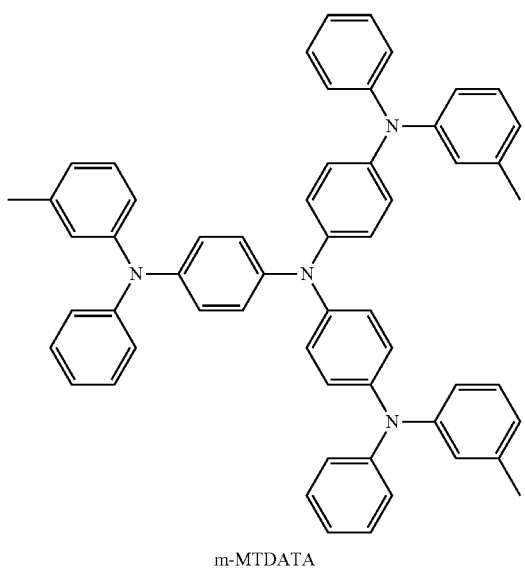

m-MTDATA

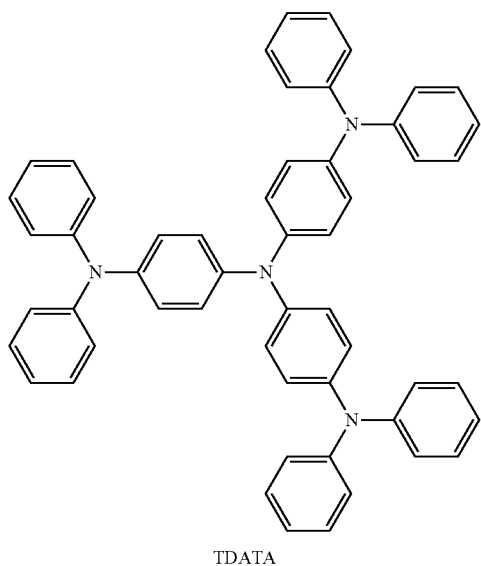

TDATA

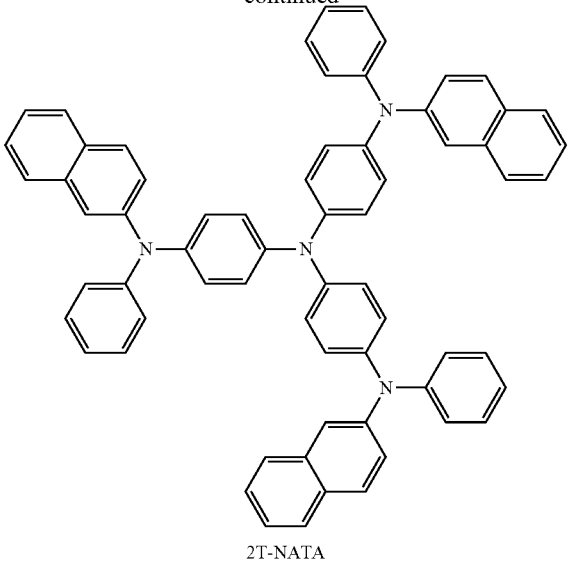

2T-NATA

As the hole transfer material, materials having high mobility for holes are suitable as materials receiving holes from an anode or a hole injection layer and transfers the holes to a light emitting layer. Specific examples thereof include arylamine-based organic materials, conductive polymers, block copolymers having conjugated parts and non-conjugated parts together, and the like, but are not limited thereto.

Examples of the hole transfer material may include known hole transfer materials including carbazole derivatives such as N-phenylcarbazole and polyvinylcarbazole, amine derivatives having an aromatic fused ring such as N,N'-bis(3-methylphenyl)-N,N'-diphenyl-[1,1-biphenyl]-4,4'-diamine (TPD) and N,N'-di(naphthalen-1-yl)-N,N'-diphenylbenzidine (α-NPD), and triphenylamine-based materials such as 4,4',4''-tris(N-carbazolyl)triphenylamine (TCTA). Among these, for example, TCTA may perform a role of preventing excitons from being spread out from a light emitting layer in addition to a role of hole transfer.

As the light emitting material, materials having favorable quantum efficiency for fluorescence or phosphorescence are preferable as materials capable of emitting light in a visible light region by receiving holes and electrons from a hole transfer layer and an electron transfer layer, respectively, and binding the holes and the electrons. Specific examples thereof include 8-hydroxy-quinoline aluminum complexes (Alq$_3$); carbazole-based compounds; dimerized styryl compounds; BAlq; 10-hydroxybenzo quinoline-metal compounds; benzoxazole-, benzothiazole- and benzimidazole-based compounds; poly(p-phenylenevinylene) (PPV)-based polymers; spiro compounds; polyfluorene, rubrene, and the like, but are not limited thereto.

The light emitting material may either include one compound or include a host and dopant combination. Examples of known hosts may include Alq$_3$, 4,4'-N,N'-dicarbazole-biphenyl (CBP), poly(n-vinylcarbazole) (PVK), 9,10-di(naphthalen-2-yl)anthracene (ADN), TCTA, 1,3,5-tris(N-phenylbenzimidazol-2-yl)benzene (TPBI), 3-tert-butyl-9,10-di(naphth-2-yl)anthracene (TBADN), E3, distyrylarylene (DSA) and the like, but are not limited thereto.

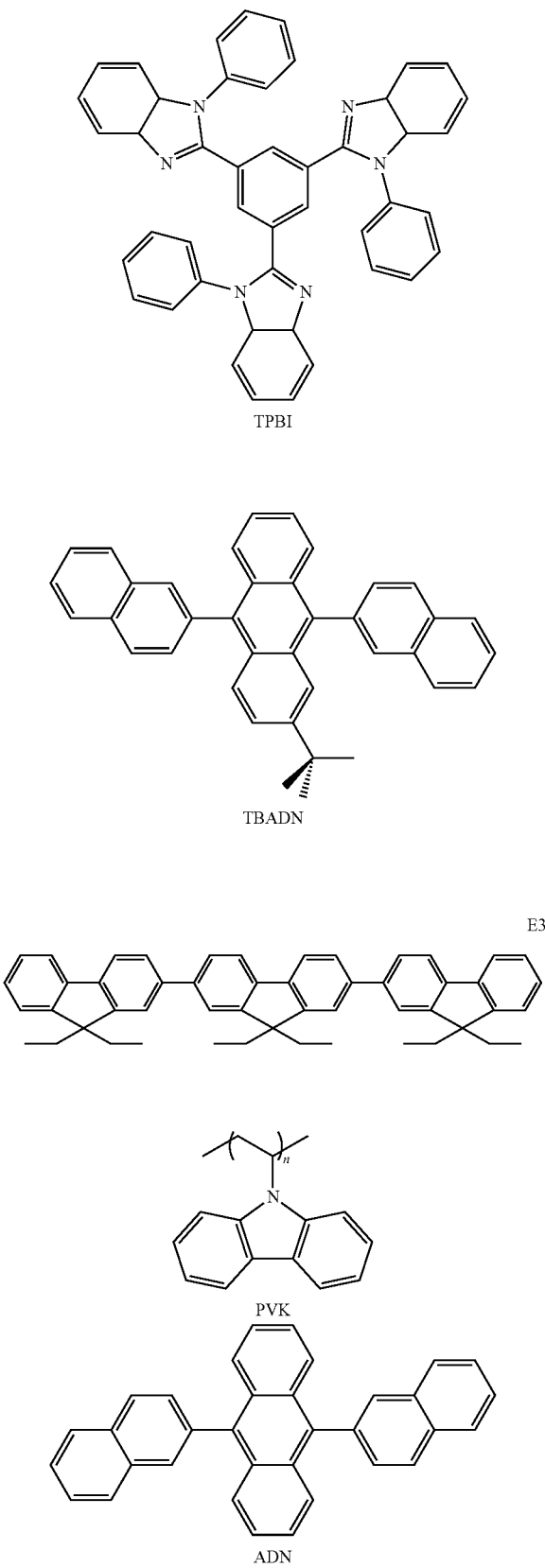
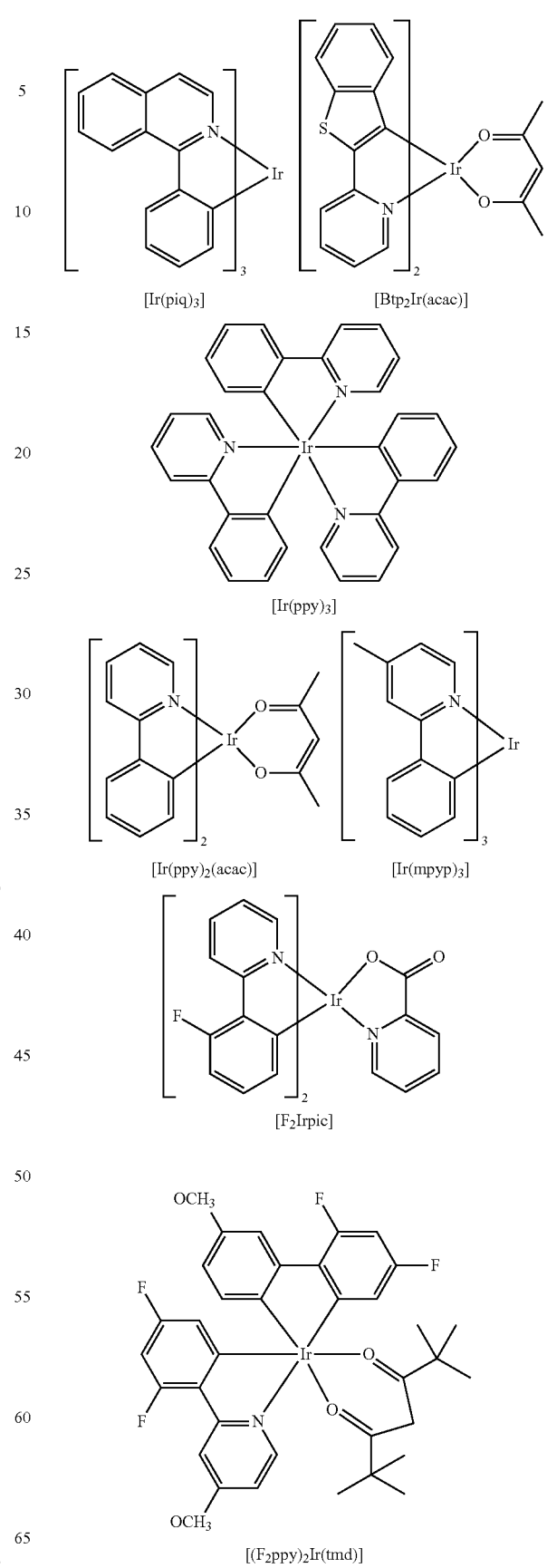
Iridium-based complexes used as the dopant are as follows.

-continued

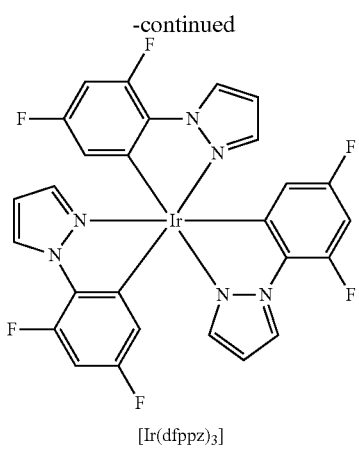

[Ir(dfppz)₃]

As the electron transfer material, materials having high mobility for electrons are suitable as materials favorably receiving electrons from a cathode and transferring the electrons to a light emitting layer. Specific examples thereof include Al complexes of 8-hydroxyquinoline; complexes including Alq₃; organic radical compounds; hydroxyflavon-metal complexes and the like, but are not limited thereto.

The capping layer (9) including the compound represented by Chemical Formula 1 as described above has a high refractive index, and therefore, may contribute to light efficiency enhancement of an organoluminescent device, particularly, to external luminescent efficiency enhancement. For example, the capping layer may have a refractive index of 1.7 to 2.4 in a wavelength of 400 nm to 700 nm.

An organoluminescent device normally has a structure in which a number of layers formed with various materials are laminated, and therefore, light produced in an organic layer may become extinct in the device by total reflection while passing through many layers in the device without being extracted to the air outside the organoluminescent device. When external luminescent efficiency, efficiency extracted outside an organoluminescent device, is low as above, total light efficiency of the organoluminescent device may decrease even when light conversion efficiency in the organic material layer is high. However, the capping layer (9) is capable of increasing efficiency of extracted outside an organoluminescent device when light produced in the organic material layer (3) progresses to the air after passing through the second electrode (4) by a principle of constructive interference, and therefore, may greatly contribute to the improvement of light efficiency of the organoluminescent device.

The organoluminescent device according to the present disclosure may be a top-emission type, a bottom-emission type or a dual-emission type depending on the materials used.

Methods for preparing the compound of Chemical Formula 1, and manufacture of an organoluminescent device using the same will be described in detail in the following examples. However, the following examples are for illustrative purposes only, and the scope of the present disclosure is not limited thereto.

<Preparation Example A> Synthesis of the Following Chemical Formula A

[Chemical Formula A]

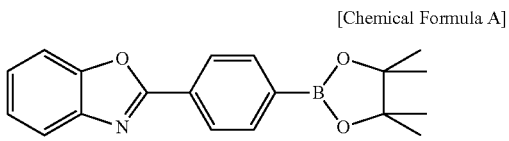 [SMILES: CC1(C)OB(c2ccc(-c3nc4ccccc4o3)cc2)OC1(C)C]

After introducing 2-(4-bromophenyl)-benzoxazole (5 g, 18.2 mmol), bis(pinacolato)diboron (5.1 g, 20.1 mmol) and potassium acetate (5.4 g, 54.7 mmol) in 1,4-dioxane (182 ml, 0.1 M) and suspension stirring the result, Pd(dppf)Cl₂ (260 mg, 0.36 mmol) was added thereto, and the result was heated and stirred for 8 hours at 100° C. After the reaction solution was cooled to room temperature, H₂O (100 ml) was added thereto, the result was stirred for 10 minutes and then extracted using THF. The water layer was removed, and the organic layer was treated with magnesium sulfate (MgSO₄) and then concentrated. The result was crystallized with ethanol (150 ml) and then filtered to obtain a compound of Chemical Formula A (5.3 g, yield 90%).

MS: [M+H]⁺=322

<Preparation Example B> Synthesis of the Following Chemical Formula B

[Chemical Formula B]

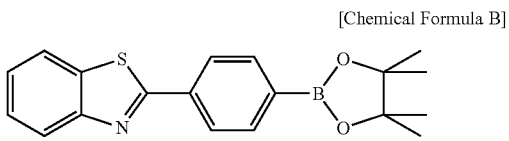 [SMILES: CC1(C)OB(c2ccc(-c3nc4ccccc4s3)cc2)OC1(C)C]

A compound of Chemical Formula B was synthesized in the same manner as the compound of Chemical Formula A except that 2-(4-bromophenyl)-benzothiazole was used instead of 2-(4-bromophenyl)-benzoxazole.

MS: [M+H]⁺=338

<Preparation Example 1> Synthesis of Chemical Formula 1-4

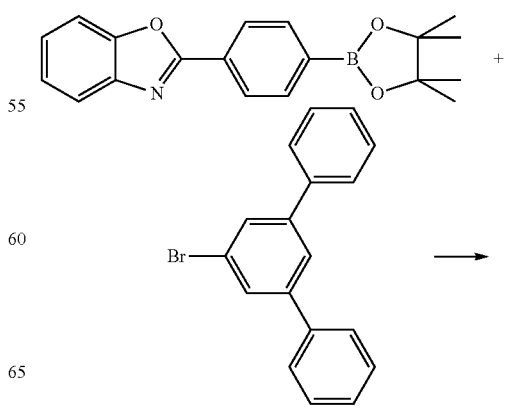

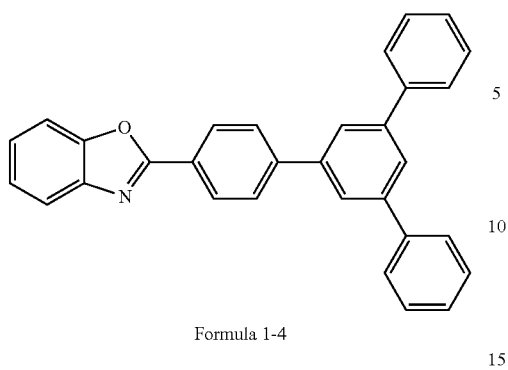

Formula 1-4

After the compound of Chemical Formula A (10 g, 31.1 mmol) and 1-bromo-3,5-diphenylbenzene (9.6 g, 31.1 mmol) were suspension stirred in THF (310 ml), $K_2CO_3$ (8.6 g, 62.3 mmol) dissolved in $H_2O$ (100 ml), and then tetrakis (triphenylphosphine) palladium(0) (720 mg, 0.62 mmol) were added thereto, and the result was refluxed for 8 hours. After the reaction was complete, the temperature was lowered to room temperature, the water layer was removed, and the organic layer was treated with magnesium sulfate ($MgSO_4$) and then filtered. The solution was vacuum concentrated under reduced pressure, and column purified with a ratio of THF/Hexane=1/3 to obtain a compound of Chemical Formula 1-4 (10 g, yield: 76%).

MS: $[M+H]^+$=424

<Preparation Example 2> Synthesis of Chemical Formula 1-7

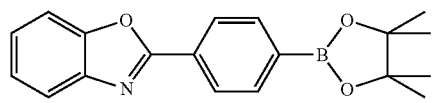

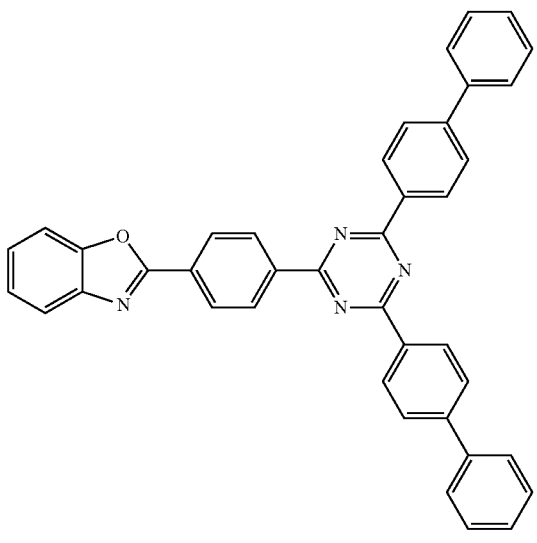

Formula 1-7

A compound of Chemical Formula 1-7 was obtained in the same manner as in the synthesis method of the compound of Chemical Formula 1-4 except that 2-chloro-4,6-bis(4-biphenylyl)-1,3,5-triazine was used instead of 1-bromo-3,5-diphenylbenzene.

MS: $[M+H]^+$=579

<Preparation Example 3> Synthesis of Chemical Formula 1-11

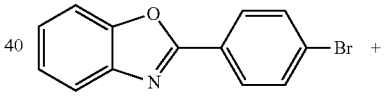

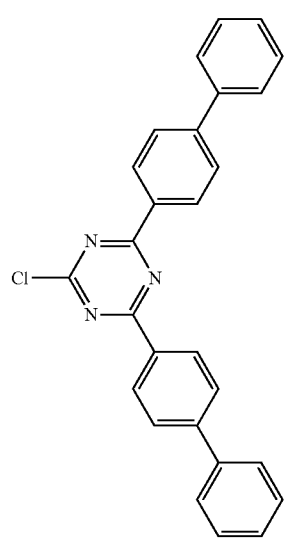

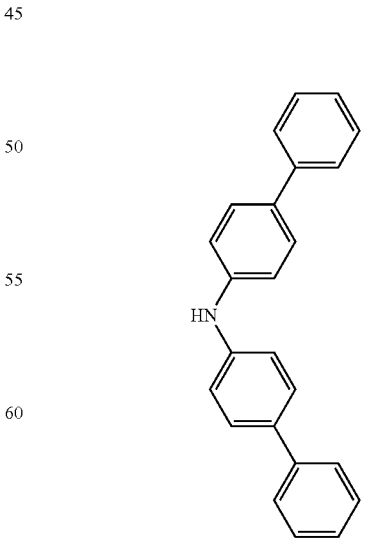

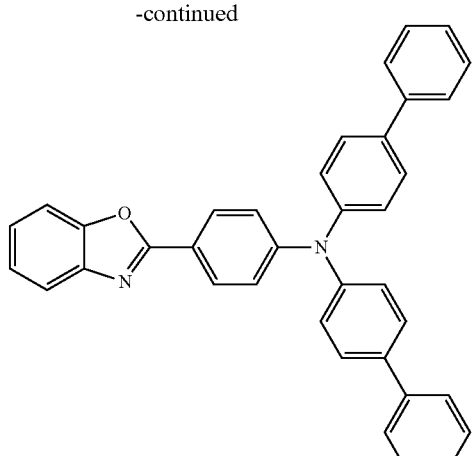

Formula 1-11

After introducing 2-(4-bromophenyl)-benzoxazole (10 g, 36.5 mmol), bis(4-biphenyl)amine (11.7 g, 36.5 mmol) and potassium acetate (10.7 g, 109.4 mmol) in toluene (360 ml) and suspension stirring the result for 10 minutes, bis(tri-tert-butylphosphine) palladium (560 mg, 1.09 mmol) was added thereto, and the result was heated and stirred for 12 hours. After the reaction was complete, the temperature was lowered to room temperature, and the result was filtered, washed several times with $H_2O$ and ethanol, and column purified with THF/hexane:1/4 to obtain a compound of Chemical Formula 1-11 (13.1 g, yield: 70%).

MS: $[M+H]^+$=515

<Preparation Example 4> Synthesis of Chemical Formula 1-28

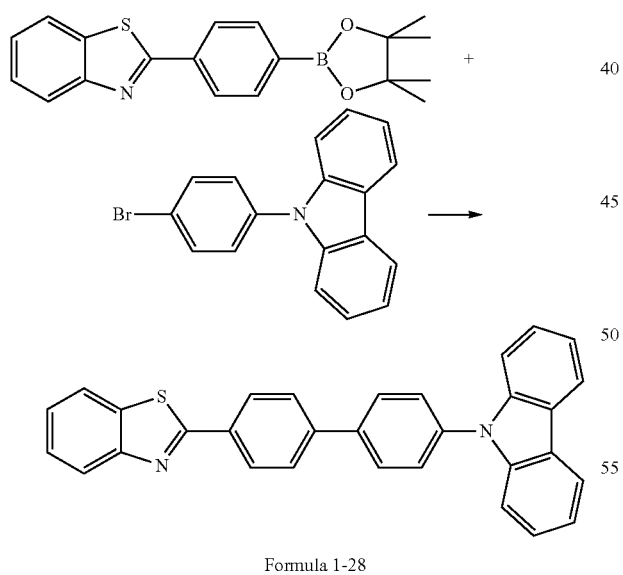

Formula 1-28

A compound of Chemical Formula 1-28 was obtained in the same manner as in the synthesis method of the compound of Chemical Formula 1-4 except that the compound of Chemical Formula B was used instead of the compound of Chemical Formula A, and 9-(4-bromophenyl)carbazole was used instead of 1-bromo-3,5-diphenylbenzene.

MS: $[M+H]^+$=453

<Preparation Example 5> Synthesis of Compound 1-34

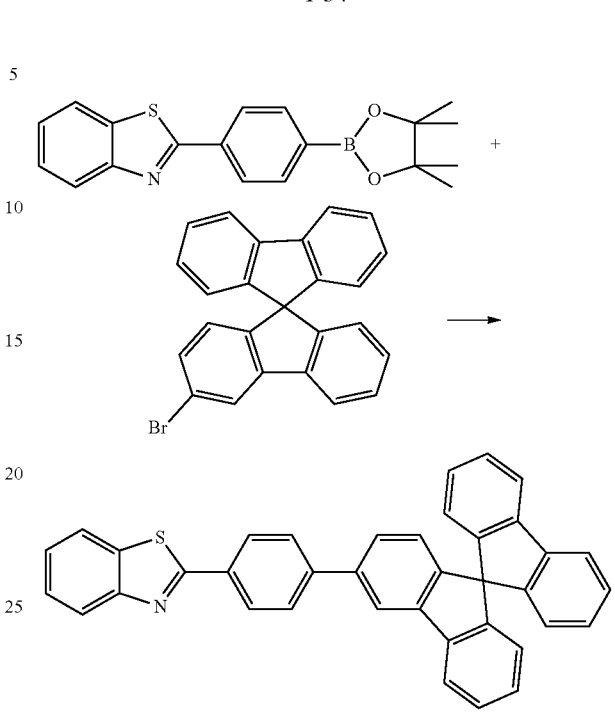

Formula 1-34

A compound of Chemical Formula 1-34 was obtained in the same manner as in the synthesis method of the compound of Chemical Formula 1-28 except that 3-bromo-9,9'-spirobi[fluorene] was used instead of 9-(4-bromophenyl)carbazole.

MS: $[M+H]^+$=526

<Preparation Example 6> Synthesis of 1-45

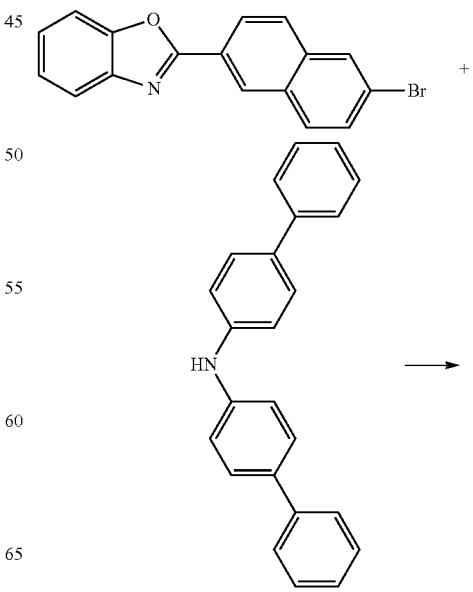

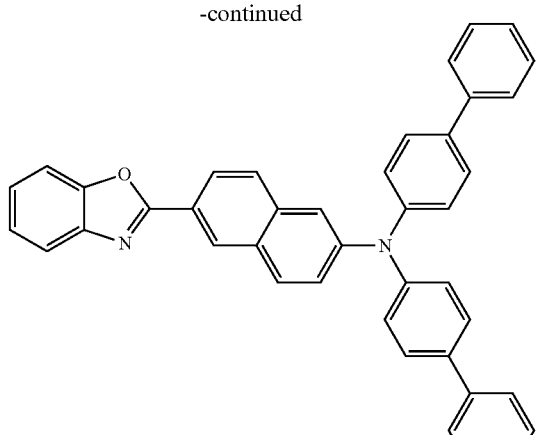

Formula 1-45

A compound of Chemical Formula 1-45 was obtained in the same manner as in the synthesis method of the compound of Chemical Formula 1-11 except that 2-(6-bromonaphthyl)-benzoxazole was used instead of 2-(4-bromophenyl)-benzoxazole.

MS: $[M+H]^+ = 565$

<Preparation Example 7> Synthesis of Compound 1-46

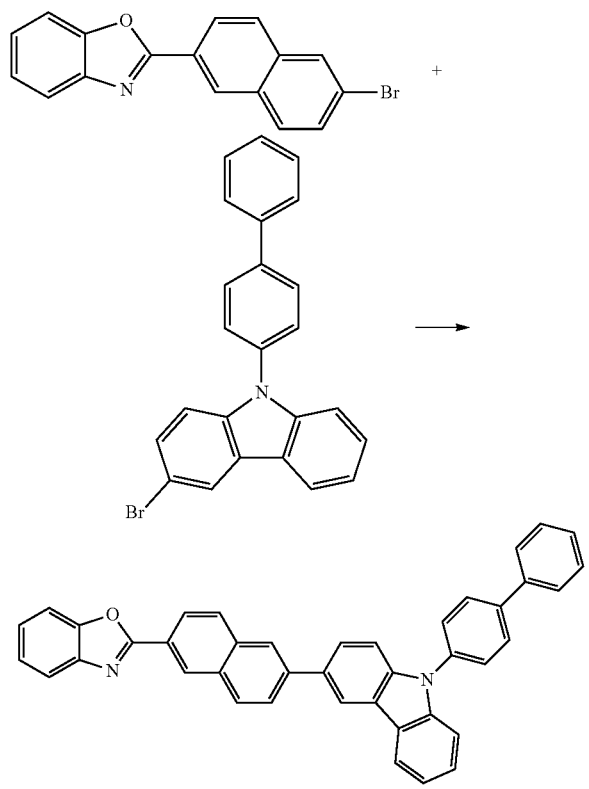

Formula 1-46

A compound of Chemical Formula 1-46 was obtained in the same manner as in the synthesis method of the compound of Chemical Formula 1-4 except that the compound of Chemical Formula C was used instead of the compound of Chemical Formula A, and 3-bromo-N-(4-biphenyl)carbazole was used instead of 1-bromo-3,5-diphenylbenzene.

MS: $[M+H]^+ = 563$

<Preparation Example 8> Synthesis of Compound 1-51

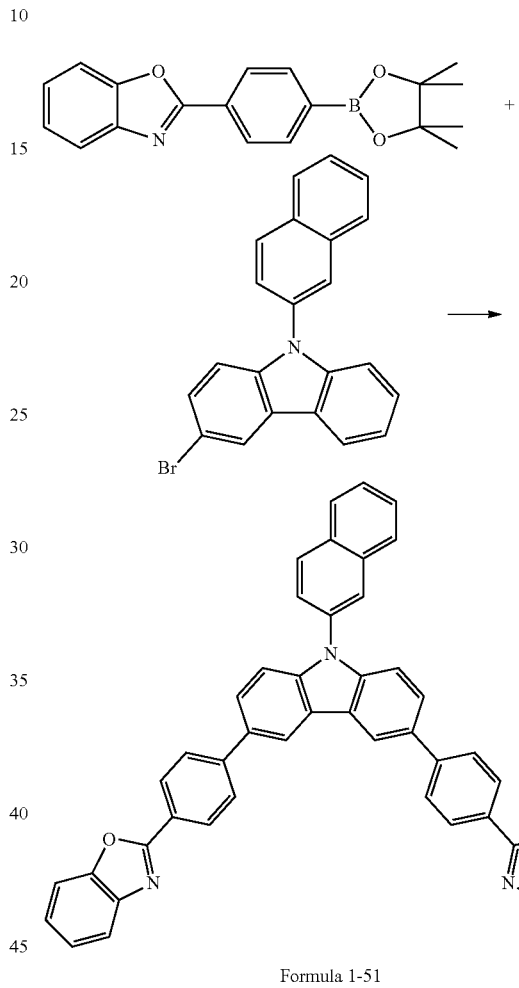

Formula 1-51

After the compound of Chemical Formula A (10 g, 31.1 mmol) and 2,6-dibromo-N-(2-naphthyl)carbazole (7.0 g, 15.6 mmol) were suspension stirred in THF (310 ml), $K_2CO_3$ (8.6 g, 62.3 mmol) dissolved in $H_2O$ (100 ml), and then tetrakis(triphenylphosphine) palladium(0) (720 mg, 0.62 mmol) were added thereto, and the result was refluxed for 8 hours. After the reaction was complete, the temperature was lowered to room temperature, the water layer was removed, and the organic layer was treated with magnesium sulfate ($MgSO_4$) and then filtered. The solution was vacuum concentrated under reduced pressure, and column purified with a ratio of THF/Hexane=1/2 to obtain a compound of Chemical Formula 1-51 (8.7 g, yield: 80%).

MS: $[M+H]^+ = 680$

Comparative Example 1

A glass substrate on which indium tin oxide (ITO) was coated as a thin film to a thickness of 1,500 Å was placed in detergent-dissolved distilled water and ultrasonic cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol, acetone and methanol, then dried, and then transferred to a plasma cleaner. Using oxygen plasma, the substrate was cleaned for 5 minutes, and then transferred to a vacuum depositor.

On the transparent ITO electrode prepared as above, a hole injection layer was formed by thermal vacuum depositing hexanitrile hexaazatriphenylene to a thickness of 500 Å. A light emitting layer was formed thereon by vacuum depositing NPB (400 Å), a material transferring holes, and then depositing Dopant D1 (4 wt %) together with the following Compound H1 (300 Å)

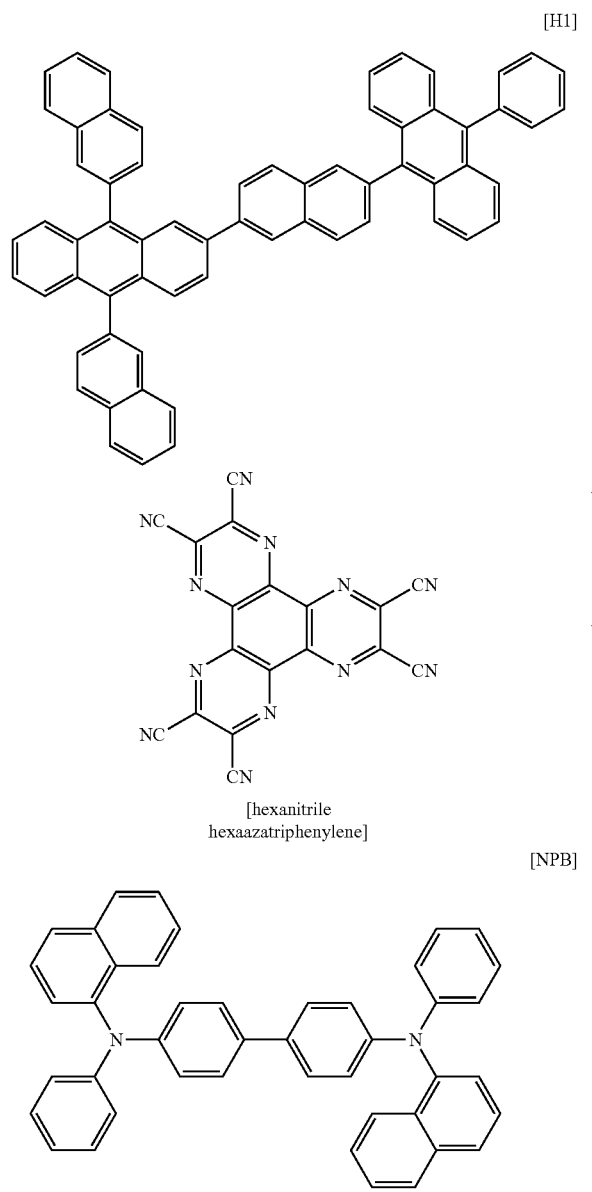

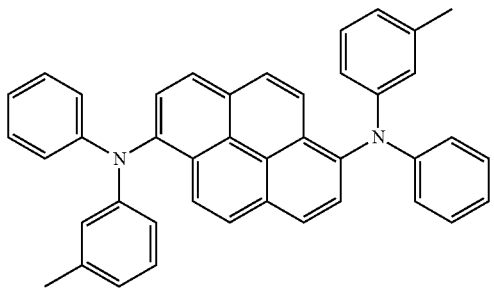

[D1]

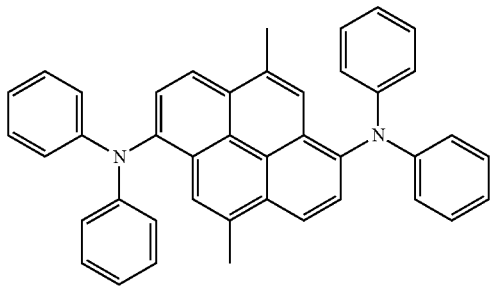

[D2]

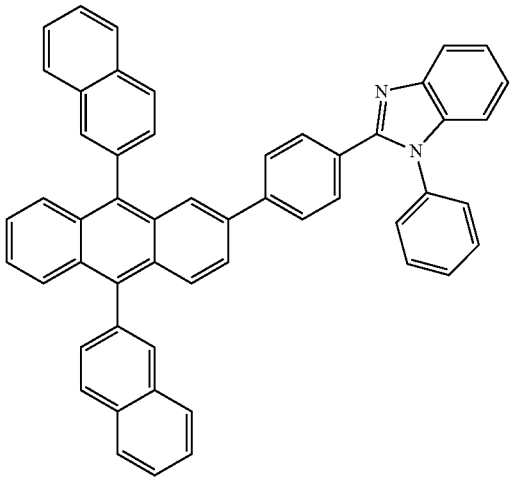

[E1]

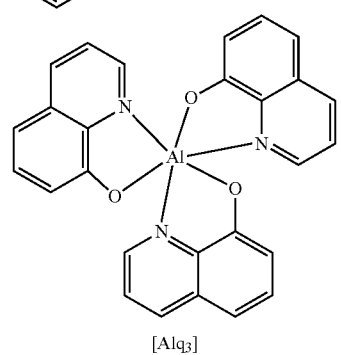

[Alq₃]

An electron injection and transfer layer was formed on the light emitting layer to a thickness of 200 Å by vacuum depositing Compound E1. A cathode was formed on the electron injection and transfer layer by depositing lithium fluoride (LiF) to a thickness of 12 Å and aluminum to a thickness of 2,000 Å in consecutive order. In the above-mentioned processes, the deposition rates of the organic materials were maintained at 1 Å/sec, and the deposition rates of the lithium fluoride and the aluminum of the cathode were maintained at 0.2 Å/sec, and 3 Å/sec to 7 Å/sec, respectively.

When applying a forward direction electric field of 7.6 V to the organoluminescent device manufactured above, blue light emission of 3.1 cd/A corresponding to x=0.154 and y=0.192 based on the 1931 CIE color coordination was observed at current density of 10 mA/cm$^2$.

Comparative Example 2

After manufacturing an organoluminescent device in the same manner as in Comparative Example 1, a capping layer was formed on the aluminum cathode by vacuum depositing Alq$_3$ to a thickness of 600 Å. When applying a forward direction electric field of 7.6 V to the organoluminescent device manufactured above, blue light emission of 4.0 cd/A corresponding to x=0.135 and y=0.098 based on the 1931 CIE color coordination was observed at current density of 9.3 mA/cm$^2$.

Test Example 1-1

After manufacturing an organoluminescent device in the same manner as in Comparative Example 1, a capping layer was formed on the aluminum cathode by vacuum depositing the Compound 1-4 to a thickness of 600 Å.

When applying a forward direction electric field of 7.6 V to the organoluminescent device manufactured above, blue light emission of 4.4 cd/A corresponding to x=0.135 and y=0.095 based on the 1931 CIE color coordination was observed at current density of 9.2 mA/cm$^2$.

Test Example 1-2

After manufacturing an organoluminescent device in the same manner as in Comparative Example 1, a capping layer was formed on the aluminum cathode by vacuum depositing the Compound 1-7 to a thickness of 600 Å.

When applying a forward direction electric field of 7.6 V to the organoluminescent device manufactured above, blue light emission of 5.3 cd/A corresponding to x=0.135 and y=0.095 based on the 1931 CIE color coordination was observed at current density of 8.5 mA/cm$^2$.

Test Example 1-3

After manufacturing an organoluminescent device in the same manner as in Comparative Example 1, a capping layer was formed on the aluminum cathode by vacuum depositing the Compound 1-11 to a thickness of 600 Å.

When applying a forward direction electric field of 7.6 V to the organoluminescent device manufactured above, blue light emission of 5.3 cd/A corresponding to x=0.135 and y=0.094 based on the 1931 CIE color coordination was observed at current density of 8.6 mA/cm$^2$.

Test Example 1-4

After manufacturing an organoluminescent device in the same manner as in Comparative Example 1, a capping layer was formed on the aluminum cathode by vacuum depositing the Compound 1-28 to a thickness of 600 Å.

When applying a forward direction electric field of 7.6 V to the organoluminescent device manufactured above, blue light emission of 5.1 cd/A corresponding to x=0.135 and y=0.095 based on the 1931 CIE color coordination was observed at current density of 8.8 mA/cm$^2$.

Test Example 1-5

After manufacturing an organoluminescent device in the same manner as in Comparative Example 1, a capping layer was formed on the aluminum cathode by vacuum depositing the Compound 1-34 to a thickness of 600 Å.

When applying a forward direction electric field of 7.7 V to the organoluminescent device manufactured above, blue light emission of 4.7 cd/A corresponding to x=0.135 and y=0.094 based on the 1931 CIE color coordination was observed at current density of 9.2 mA/cm$^2$.

Test Example 1-6

After manufacturing an organoluminescent device in the same manner as in Comparative Example 1, a capping layer was formed on the aluminum cathode by vacuum depositing the Compound 1-45 to a thickness of 600 Å.

When applying a forward direction electric field of 7.7 V to the organoluminescent device manufactured above, blue light emission of 5.4 cd/A corresponding to x=0.135 and y=0.094 based on the 1931 CIE color coordination was observed at current density of 8.5 mA/cm$^2$.

Test Example 1-7

After manufacturing an organoluminescent device in the same manner as in Comparative Example 1, a capping layer was formed on the aluminum cathode by vacuum depositing the Compound 1-46 to a thickness of 600 Å.

When applying a forward direction electric field of 7.6 V to the organoluminescent device manufactured above, blue light emission of 5.2 cd/A corresponding to x=0.135 and y=0.094 based on the 1931 CIE color coordination was observed at current density of 8.6 mA/cm$^2$.

Test Example 1-8

After manufacturing an organoluminescent device in the same manner as in Comparative Example 1, a capping layer was formed on the aluminum cathode by vacuum depositing the Compound 1-51 to a thickness of 600 Å.

When applying a forward direction electric field of 7.6 V to the organoluminescent device manufactured above, blue light emission of 5.6 cd/A corresponding to x=0.135 and y=0.095 based on the 1931 CIE color coordination was observed at current density of 8.3 mA/cm$^2$.

As seen from the test results, it can be seen that luminescent efficiency and color purity may be significantly improved in an organic electronic light emitting device using the compounds according to the present disclosure as a capping layer. By using the compounds of the present disclosure having a higher refractive index compared to a refractive index of Alq$_3$ (1.5 to 1.6), performance of an organoluminescent device is capable of being improved, and this organoluminescent device is capable of being used in industrial products.

The invention claimed is:
1. An organoluminescent device comprising:
a first electrode;
a second electrode;
one or more organic material layers disposed between the first electrode and the second electrode; and a capping layer provided on a surface of the first electrode or the second electrode, which is opposite to a surface facing the organic material layers, and the capping layer is an outmost layer of the organoluminescent device, wherein the capping layer includes a compound represented by the following Chemical Formula 1:

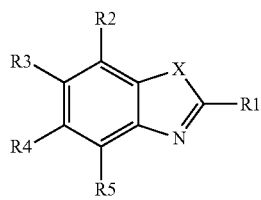

[Chemical Formula 1]

wherein, in Chemical Formula 1,
X is O or S;
R1 is represented by -(L1)p-A1;
L1 is a direct bond; or an unsubstituted arylene group;
p is an integer of 0 to 10;
when p is 2 or greater, L1s are the same as or different from each other;
A1 is an amine group substituted with an aryl group or an alkylaryl group, wherein the aryl group and the alkylaryl group are each independently unsubstituted or substituted with one or more substituents selected from the group consisting of an alkyl group, an unsubstituted aryl group, and a heterocyclic group;
an aryl group which is unsubstituted or substituted with one or more substituents selected from the group consisting of an alkyl group, an aryl group, and a heterocyclic group;
or a heterocyclic group which is unsubstituted or substituted with one or more substituents selected from the group consisting of an alkyl group, an aryl group, and a heterocyclic group;
R2 to R5 are the same as or different from each other, and each independently represented by -(L2)q-A2, and optionally adjacent groups of R2 to R5 bond to each other to form a substituted or unsubstituted ring;
L2 is a direct bond; or an unsubstituted arylene group;
q is an integer of 0 to 10;
when q is 2 or greater, L2s are the same as or different from each other; and
A2 is hydrogen; deuterium; an aryl group which is unsubstituted or substituted with one or more substituents selected from the group consisting of an alkyl group, an aryl group, and a heterocyclic group; or a heterocyclic group which is unsubstituted or substituted with one or more substituents selected from the group consisting of an alkyl group, an aryl group, and a heterocyclic group,
provided that when R2 to R5 are each hydrogen, then A1 is an aryl group which is unsubstituted or substituted with one or more substituents selected from the group consisting of an unsubstituted alkyl group, and an unsubstituted aryl group; or a heterocyclic group which is unsubstituted or substituted with one or more substituents selected from the group consisting of an alkyl group, an aryl group, and a heterocyclic group, wherein the heterocyclic group contained in A1 is a pyridyl group, a pyrrole group, pyrimidyl group, a pyridazinyl group, a furanyl group, a thiophenyl group, an imidazole group, a pyrazole group, an oxazole group, an isoxazole group, a thiazole group, an isothiazole group, a triazole group, an oxadiazole group, a thiadiazole group, a dithiazole group, a tetrazole group, a pyranyl group, a thiopyranyl group, a pyrazinyl group, an oxazinyl group, a thiazinyl group, a dioxinyl group, a triazinyl group, a tetrazinyl group, a quinolinyl group, an isoquinolinyl group, a quinolyl group, a quinazolinyl group, a quinoxalinyl group, a naphthyridinyl group, an acridyl group, a xanthenyl group, a phenanthridinyl group, a diazanaphthalenyl group, a triazaindenyl group, an indole group, an indolinyl group, an indolizinyl group, a phthalazinyl group, a pyridopyrimidinyl group, a pyridopyrazinyl group, a pyrazinopyrazinyl group, a benzimidazole group, a benzothiophene group, a benzofuranyl group, a dibenzothiophenyl group, a dibenzofuranyl group, a N-substituted carbazole group where the N atom of the carbazole is substituted, a benzocarbazole group, a dibenzocarbazole group, an indolocarbazole group, an indenocarbazole group, a phenazinyl group, an imidazopyridine group, a phenoxazinyl group, a phenanthridine group, a phenanthroline group, a phenothiazine group, an imidazopyridine group, an imidazophenanthridine group, a benzimidazoquinazoline group, or a benzimidazophenanthridine group,
provided that L1 and L2 do not include an anthracenylene group, and A1 and A2 do not include an anthracenyl group.

2. The organoluminescent device of claim 1, wherein Chemical Formula 1 is represented by Chemical Formula 2:

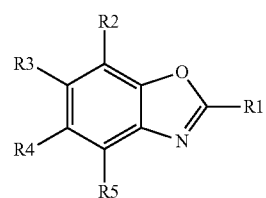

[Chemical Formula 2]

wherein, in Chemical Formula 2,
definitions of R1 to R5 are the same as in Chemical Formula 1.

3. The organoluminescent device of claim 1, wherein the compound of Chemical Formula 1 is represented by any one of Chemical Formula 4 to Chemical Formula 11:

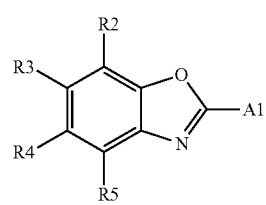

[Chemical Formula 4]

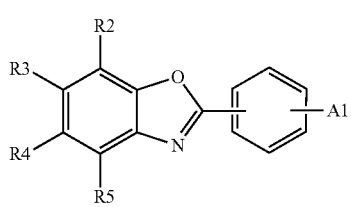

[Chemical Formula 5]

[Chemical Formula 6]

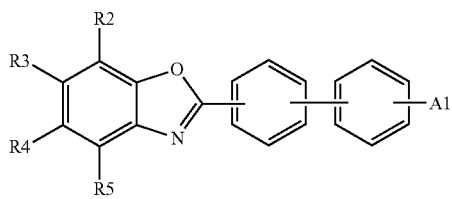

[Chemical Formula 7]

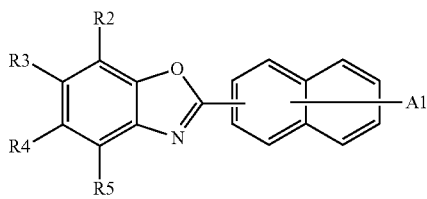

[Chemical Formula 8]

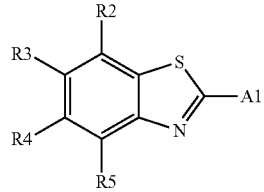

[Chemical Formula 9]

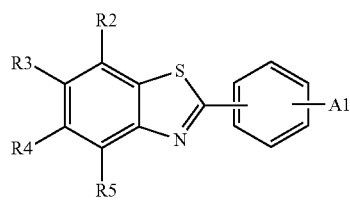

[Chemical Formula 10]

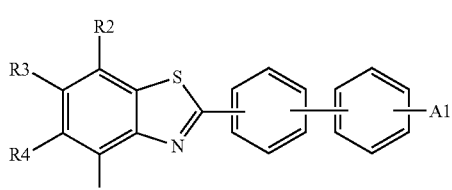

[Chemical Formula 11]

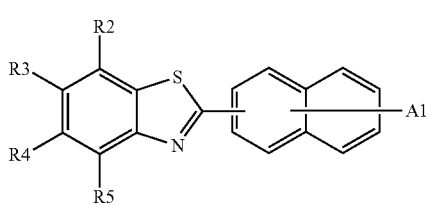

wherein, in Chemical Formula 4 to Chemical Formula 11, definitions of R2 to R5 and A1 are the same as in Chemical Formula 1.

4. The organoluminescent device of claim 1, wherein the compound of Chemical Formula 1 is represented by any one of Chemical Formula 12 to Chemical Formula 19:

[Chemical Formula 12]

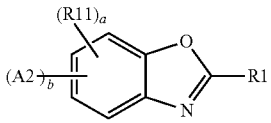

[Chemical Formula 13]

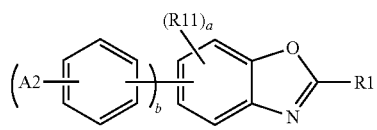

[Chemical Formula 14]

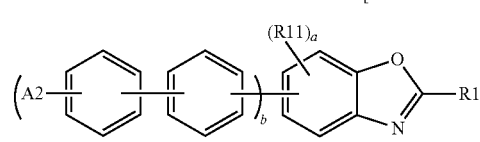

[Chemical Formula 15]

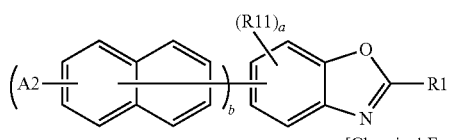

[Chemical Formula 16]

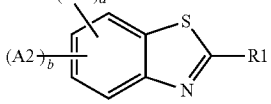

[Chemical Formula 17]

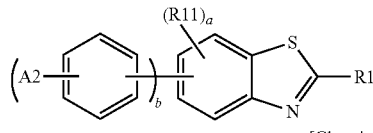

[Chemical Formula 18]

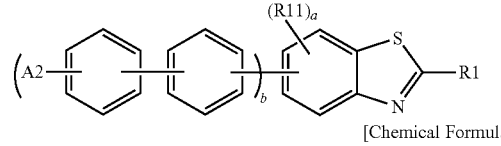

[Chemical Formula 19]

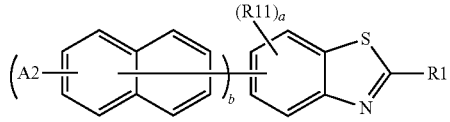

wherein, in Chemical Formula 12 to Chemical Formula 19,

R11 has the same definition as R2 to R5 in Chemical Formula 1;

definitions of R1 and A2 are the same as in Chemical Formula 1;

a and b are the same as or different from each other, and each independently represent an integer of 0 to 4; and a+b is 4, provided that when b is 0 and R11 is hydrogen, then A1 is an aryl group which is unsubstituted or substituted with one or more substituents selected from the group consisting of an unsubstituted alkyl group, and an unsubstituted aryl group; or a heterocyclic group which is unsubstituted or substituted with one or more substituents selected from the group consisting of an alkyl group, an aryl group, and a heterocyclic group, wherein the heterocyclic group contained in A1 is a pyridyl group, a pyrrole group, pyrimidyl group, a pyridazinyl group, a furanyl group, a thiophenyl group, an imidazole group, a pyrazole group, an oxazole group, an isoxazole group, a thiazole group, an isothiazole group, a triazole group, an oxadiazole group, a thiadiazole group, a dithiazole group, a tetrazole group, a pyranyl group, a thiopyranyl group, a pyrazinyl group, an oxazinyl group, a thiazinyl group, a dioxinyl group, a triazinyl group, a tetrazinyl group, a quinolinyl group, an isoquinolinyl group, a quinolyl group, a quinazolinyl group, a quinoxalinyl group, a naphthyridinyl group, an acridyl group, a xanthenyl group, a phenanthridinyl group, a diazanaphthalenyl group, a triazaindenyl group, an indole group, an indolinyl group, an indolizinyl group, a phthalazinyl group, a pyridopyrimidinyl group, a pyridopyrazinyl group, a pyrazinopyrazinyl group, a benzimidazole group, a benzothiophene group, a benzofuranyl group, a dibenzothiophenyl group, a dibenzofuranyl group, a N-substituted carbazole group where the N atom of the carbazole is substituted, a benzocarbazole group, a dibenzocarbazole group, an indolocarbazole group, an indenocarbazole group, a phenazinyl group, an imidazopyridine group, a phenoxazinyl group, a phenanthridine group, a phenanthroline group, a phenothiazine group, an imidazopyridine group, an imidazophenanthridine group, a benzimidazoquinazoline group, or a benzimidazophenanthridine group.

5. The organoluminescent device of claim 1, wherein the compound of Chemical Formula 1 is any one selected from among the following structures:

Formula 1-1

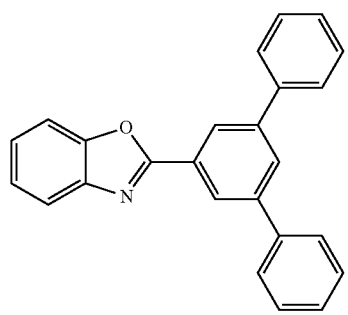

Formula 1-2

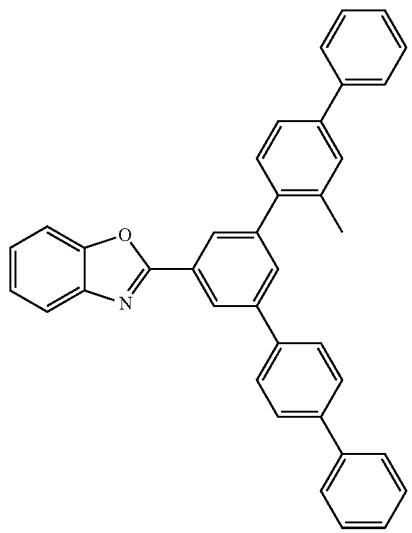

Formula 1-3

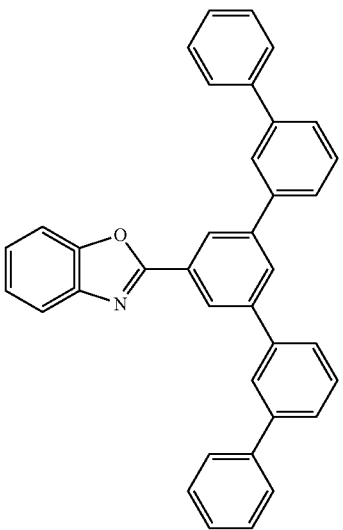

Formula 1-4

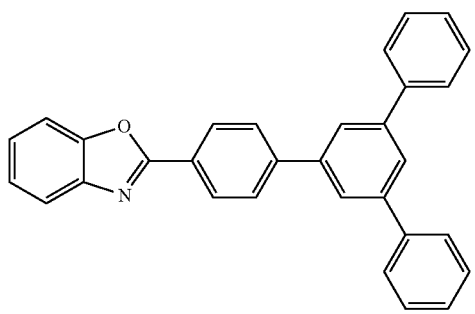

Formula 1-5

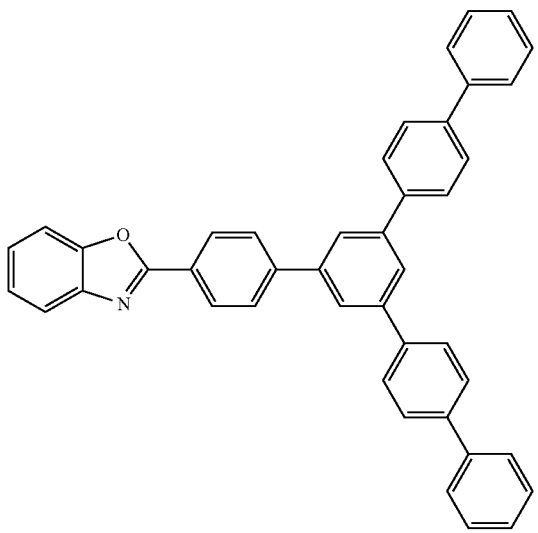

Formula 1-6
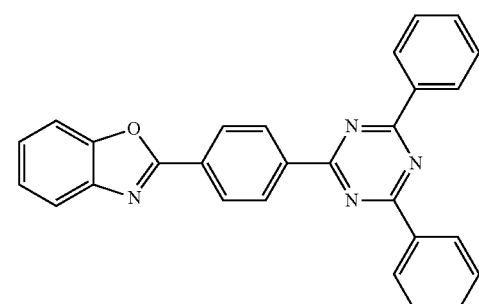
Formula 1-7
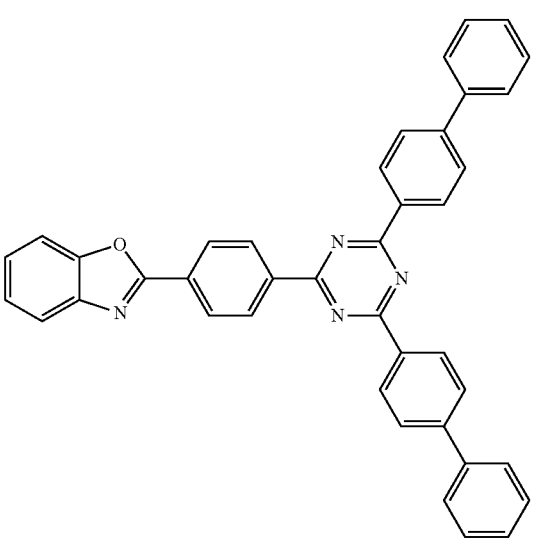
Formula 1-8
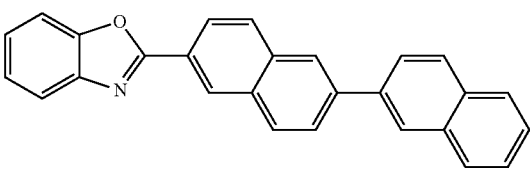
Formula 1-9
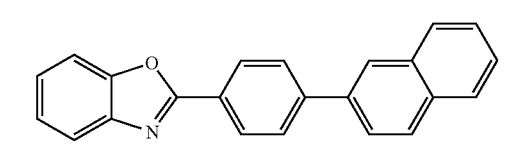
Formula 1-10
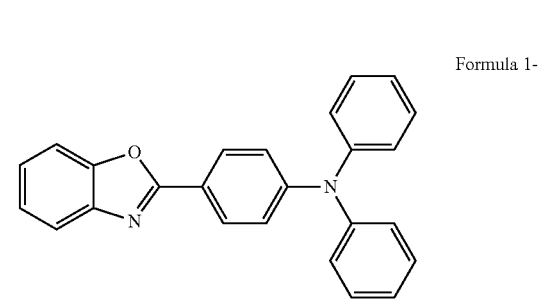
Formula 1-11
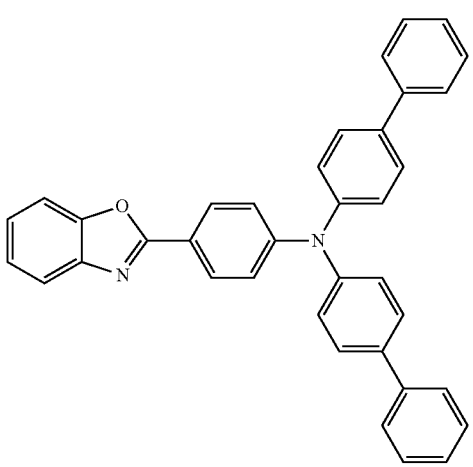
Formula 1-12
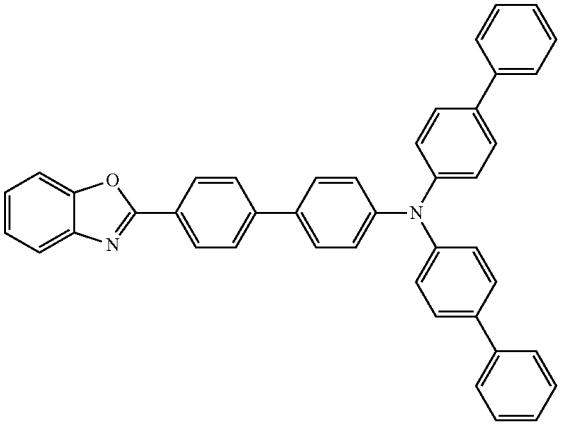
Formula 1-13
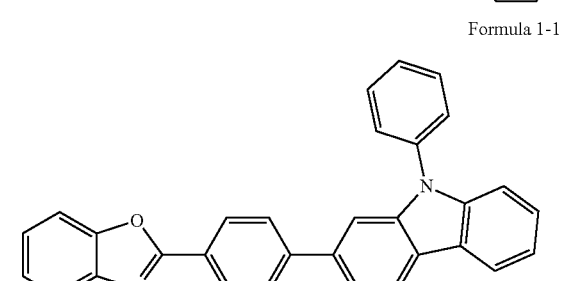
Formula 1-14
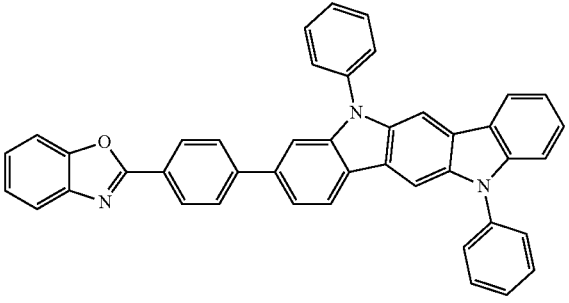

Formula 1-15
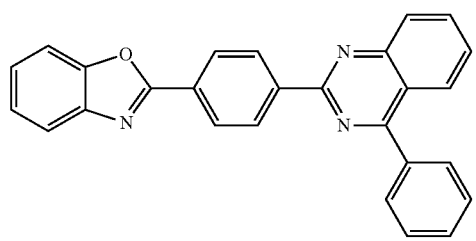
Formula 1-16
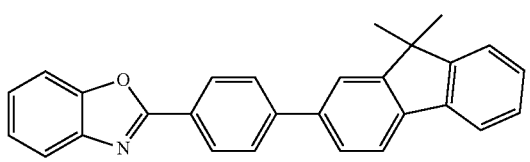
Formula 1-17
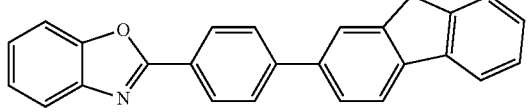
Formula 1-18
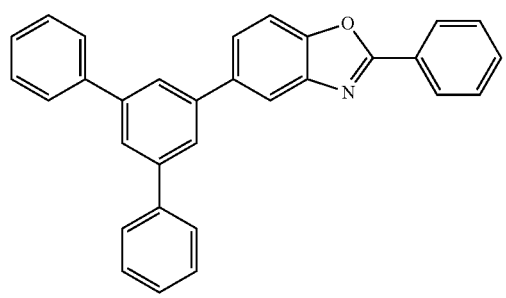
Formula 1-19
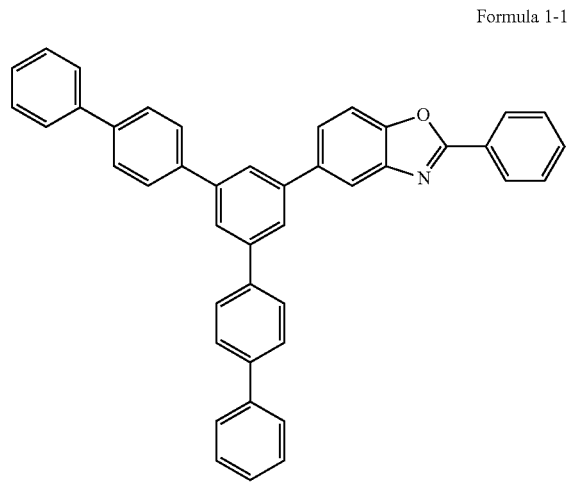
Formula 1-20
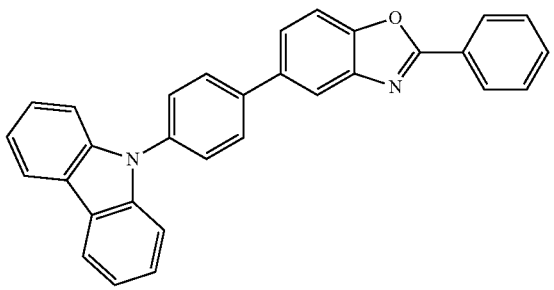
Formula 1-21
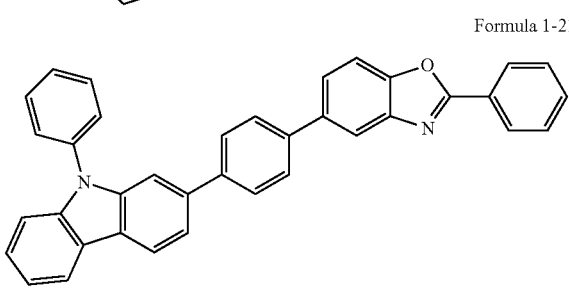
Formula 1-22
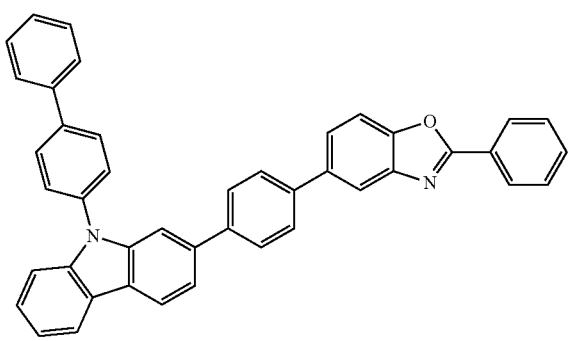
Formula 1-23
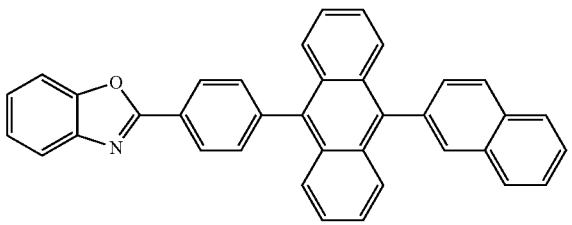
Formula 1-24
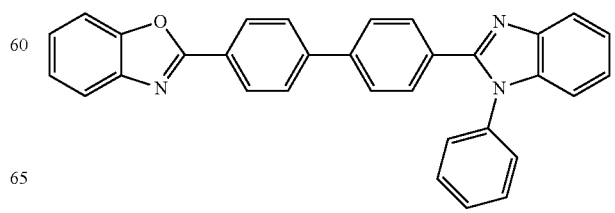

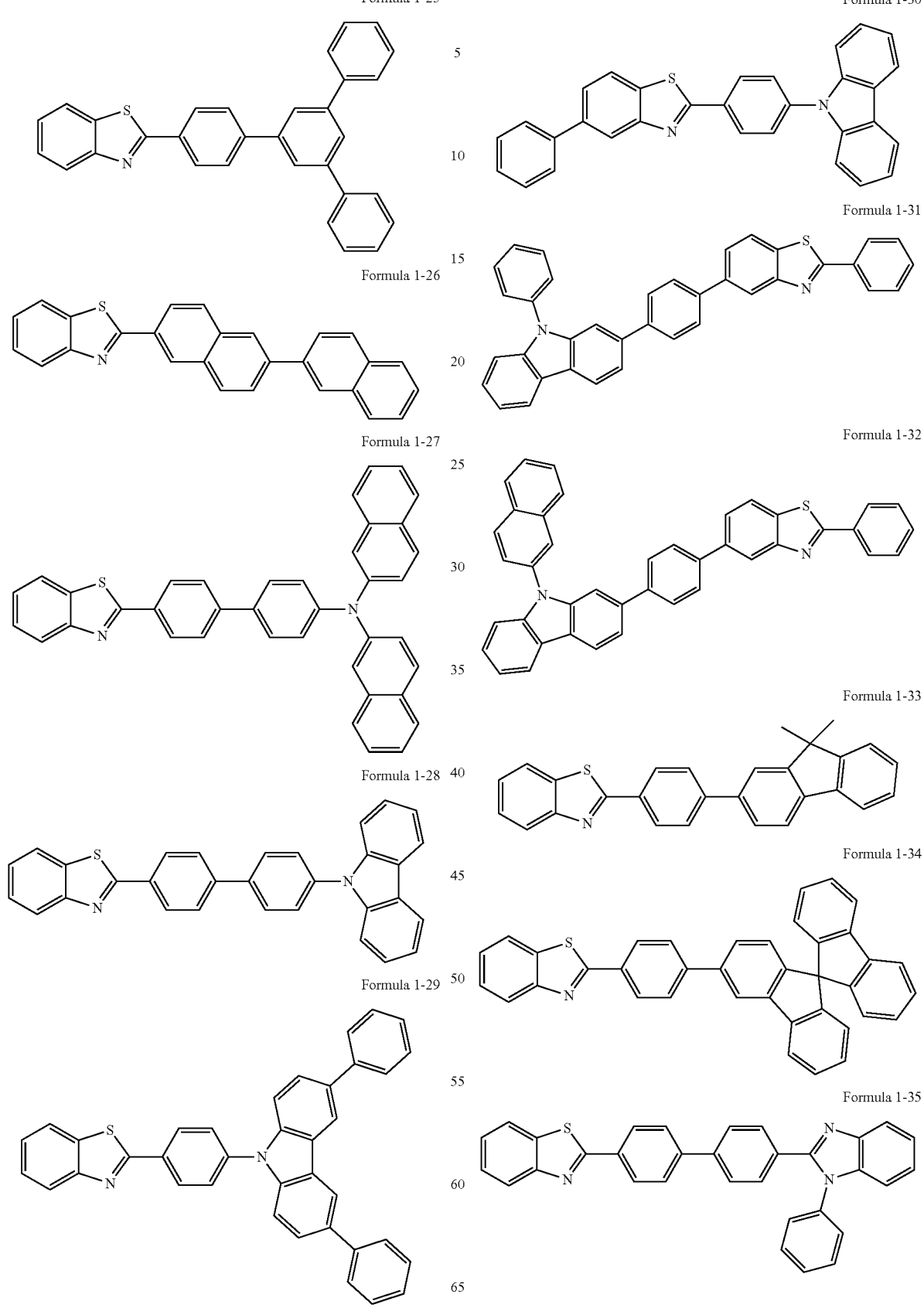

Formula 1-36
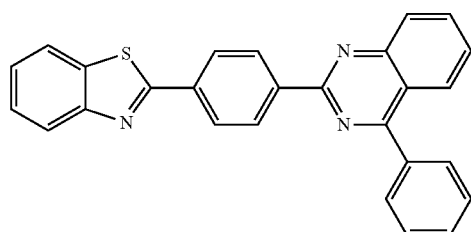
Formula 1-37
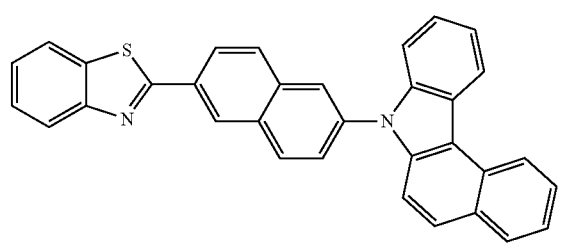
Formula 1-38
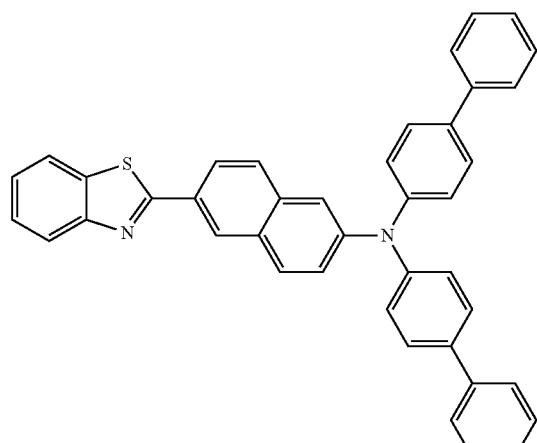
Formula 1-39
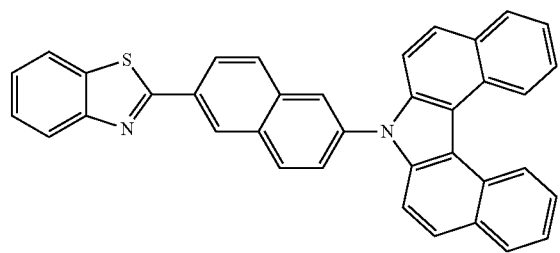
Formula 1-40
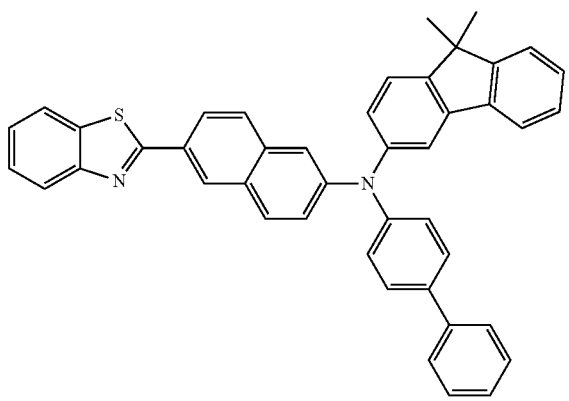
Formula 1-41
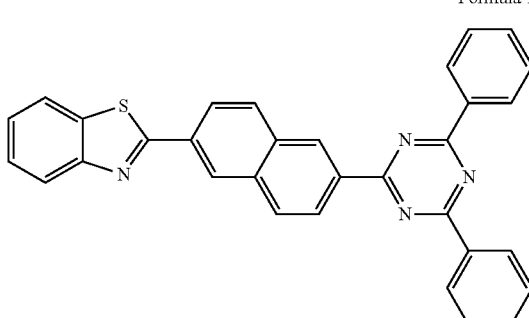
Formula 1-42
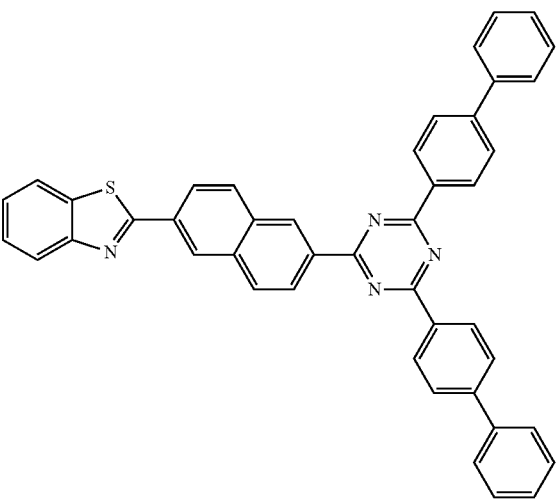
Formula 1-43
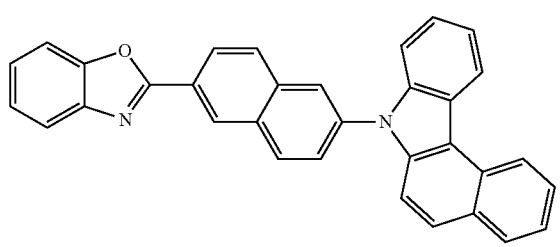

Formula 1-44
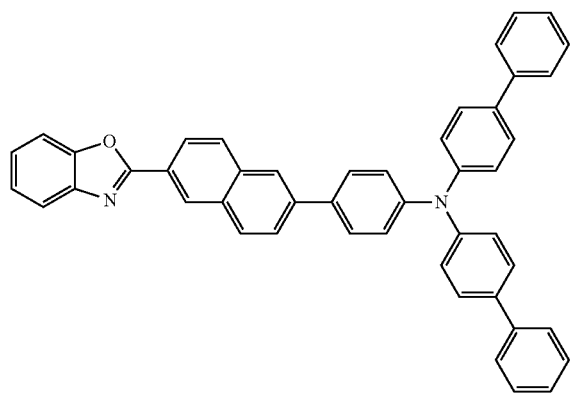
Formula 1-45
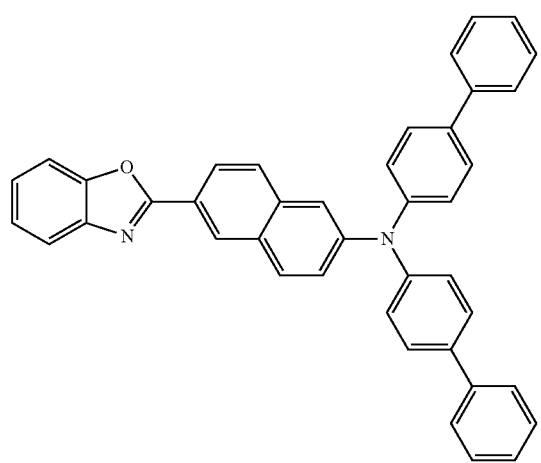
Formula 1-46
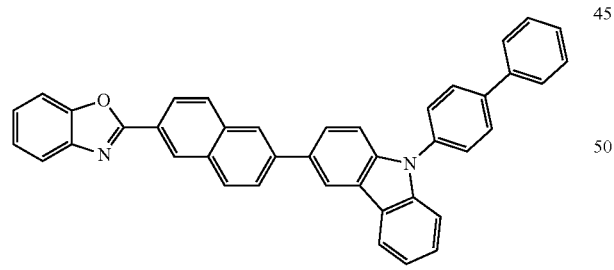
Formula 1-47
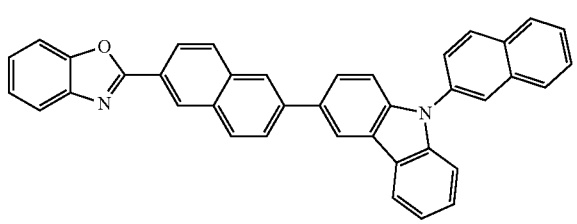
Formula 1-48
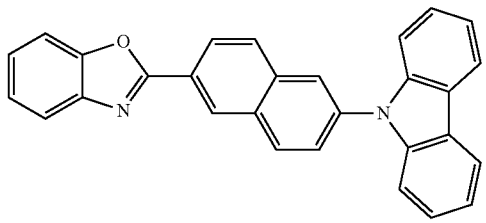
Formula 1-49
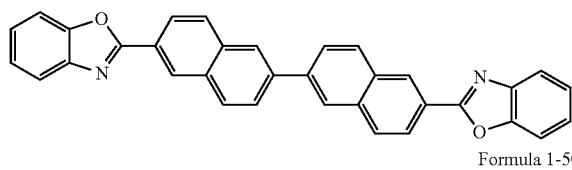
Formula 1-50
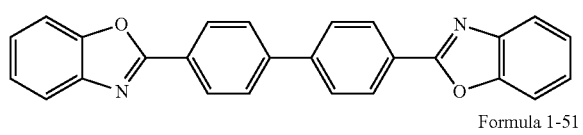
Formula 1-51
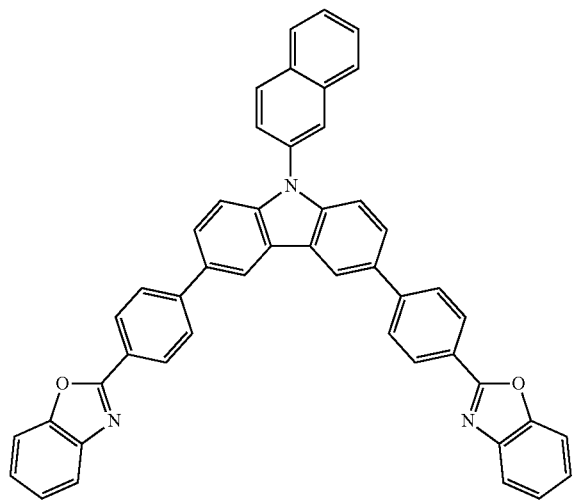
Formula 1-52
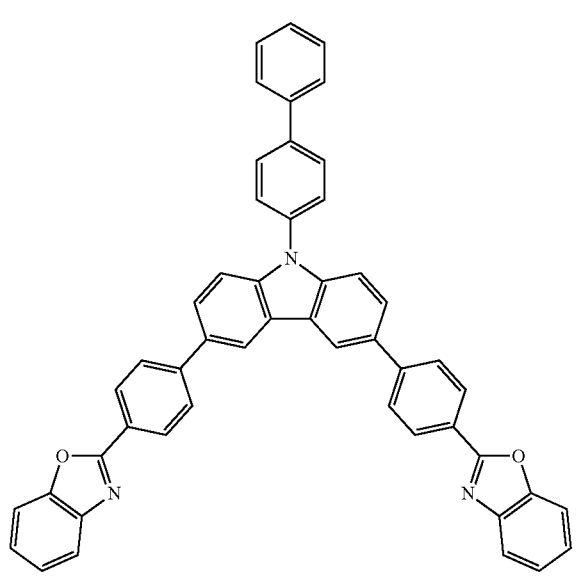

Formula 1-53

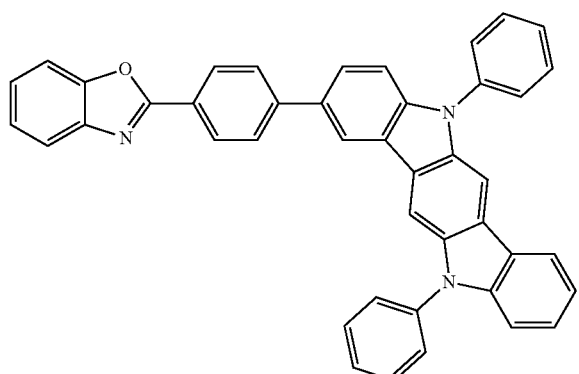

Formula 1-54

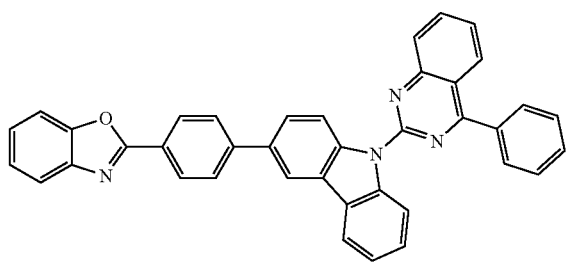

Formula 1-55

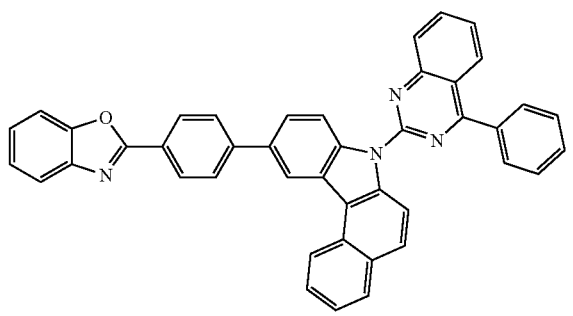

Formula 1-56

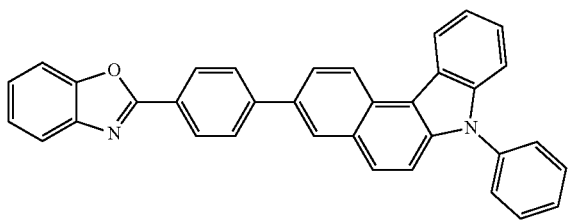

Formula 1-57

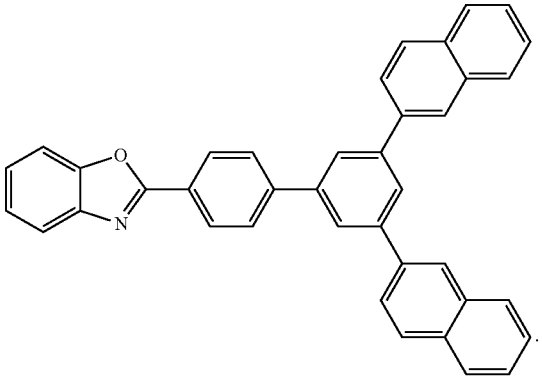

6. The organoluminescent device of claim 1, wherein the organic material layer includes a light emitting layer.

7. The organoluminescent device of claim 6, wherein the organic material layer includes one or more layers of an electron injection layer, an electron transfer layer, a hole injection layer, a hole transfer layer, or a layer carrying out hole injection and hole transfer at the same time.

8. The organoluminescent device of claim 1, wherein the organic material layer includes a light emitting layer, and the light emitting layer includes a compound represented by the following Chemical Formula A-1:

[Chemical Formula A-1]

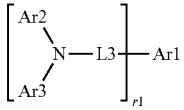

wherein, in Chemical Formula A-1, r1 is an integer of 1 or greater;

Ar1 is a substituted or unsubstituted monovalent or higher benzofluorene group; a substituted or unsubstituted monovalent or higher fluoranthene group; a substituted or unsubstituted monovalent or higher pyrene group; or a substituted or unsubstituted monovalent or higher chrysene group;

L3 is a direct bond; a substituted or unsubstituted arylene group; or a substituted or unsubstituted heteroarylene group;

Ar2 and Ar3 are the same as or different from each other, and each independently represent a substituted or unsubstituted aryl group; a substituted or unsubstituted silyl group; a substituted or unsubstituted alkyl group; a substituted or unsubstituted arylalkyl group; or a substituted or unsubstituted a heteroaryl group, and optionally Ar2 and Ar3 bond to each other to form a substituted or unsubstituted ring; and when r1 is 2 or greater, structures in the parentheses are the same as or different from each other.

9. The organoluminescent device of claim 8, wherein L3 is a direct bond, Ar1 is a substituted or unsubstituted divalent pyrene group, Ar2 and Ar3 are the same as or different from each other and each independently represent an aryl group unsubstituted or substituted with an alkyl group, and r1 is 2.

10. The organoluminescent device of claim 1, wherein the organic material layer includes a light emitting layer, and the light emitting layer includes a compound represented by the following Chemical Formula A-2:

[Chemical Formula A-2]

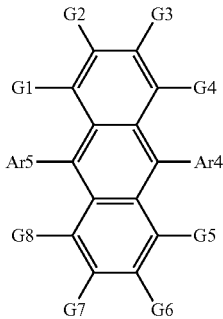

wherein, in Chemical Formula A-2,

Ar4 and Ar5 are the same as or different from each other, and each independently represent a substituted or unsubstituted monocyclic aryl group; or a substituted or unsubstituted multicyclic aryl group; and G1 to G8 are the same as or different from each other, and each independently represent hydrogen; a substituted or unsubstituted monocyclic aryl group; or a substituted or unsubstituted multicyclic aryl group.

11. The organoluminescent device of claim 10, wherein Ar4 and Ar5 are a 2-naphthyl group, and G1 to G8 are the same as or different from each other, and each independently represent hydrogen; or a substituted or unsubstituted multicyclic aryl group.

12. The organoluminescent device of claim 8, wherein the light emitting layer further includes a compound represented by the following Chemical Formula A-2:

[Chemical Formula A-2]

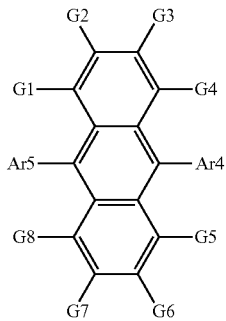

wherein, in Chemical Formula A-2,

Ar4 and Ar5 are the same as or different from each other, and each independently represent a substituted or unsubstituted monocyclic aryl group; or a substituted or unsubstituted multicyclic aryl group; and G1 to G8 are the same as or different from each other, and each independently represent hydrogen; a substituted or unsubstituted monocyclic aryl group; or a substituted or unsubstituted multicyclic aryl group.

13. The organoluminescent device of claim 1, wherein R1 is an unsubstituted phenyl group.

14. The organoluminescent device of claim 1, wherein at least one of R2 to R5 is not hydrogen or deuterium.

15. The organoluminescent device of claim 1, wherein at least one of R2 to R5 is not hydrogen.

* * * * *